United States Patent
Meng et al.

(10) Patent No.: US 10,136,838 B2
(45) Date of Patent: Nov. 27, 2018

(54) PERSONAL SPIROMETER

(71) Applicant: PMD Healthcare, Allentown, PA (US)

(72) Inventors: Wayne Meng, Fogelsville, PA (US); Glenn Allen Straub, Fogelsville, PA (US); William John Roehner, Warrington, PA (US); Paul Meredith Crawn, Ottsville, PA (US)

(73) Assignee: PMD Healthcare, Lansdale, PA (US)

( * ) Notice: Subject to any disclaimer, the term of this patent is extended or adjusted under 35 U.S.C. 154(b) by 985 days.

(21) Appl. No.: 14/356,273

(22) PCT Filed: Nov. 5, 2012

(86) PCT No.: PCT/US2012/063551
§ 371 (c)(1),
(2) Date: May 5, 2014

(87) PCT Pub. No.: WO2013/067495
PCT Pub. Date: May 10, 2013

(65) Prior Publication Data
US 2014/0316296 A1     Oct. 23, 2014

Related U.S. Application Data

(60) Provisional application No. 61/555,235, filed on Nov. 3, 2011.

(51) Int. Cl.
*A61B 5/08*     (2006.01)
*A61B 5/09*     (2006.01)
(Continued)

(52) U.S. Cl.
CPC .............. *A61B 5/09* (2013.01); *A61B 5/0004* (2013.01); *A61B 5/0022* (2013.01); *A61B 5/486* (2013.01);
(Continued)

(58) Field of Classification Search
CPC ......... A61B 5/087; A61B 5/0971; A61B 5/09; A61B 5/091
See application file for complete search history.

(56) References Cited

U.S. PATENT DOCUMENTS

| 5,277,195 A | 1/1994 | Williams |
| 5,333,106 A | 7/1994 | Lanpher et al. |

(Continued)

FOREIGN PATENT DOCUMENTS

| CN | 101426424   | 5/2009 |
| CN | 101678184 A | 3/2010 |

(Continued)

OTHER PUBLICATIONS

The International Search Report for corresponding PCT Application No. PCT/US12/63551 dated Jul. 10, 2013, 6 pages.

(Continued)

*Primary Examiner* — Christian Jang
(74) *Attorney, Agent, or Firm* — FisherBroyles LLP

(57) ABSTRACT

A spirometer for correlating test results with other user date to indicate a relationship, said spirometer comprising: (a) a processor; (b) memory operatively connected to said processor and configured with instruction to instruct the processor to perform the following steps: (i) recording spirometer results of a user; (ii) correlating said results with user data, said user data comprising at least one of a medication log, a medical diary, a baseline performance for said user provided by a healthcare provider, or other results from other testing devices; and (iii) indicating a relationship between said results and said user data.

14 Claims, 13 Drawing Sheets

(51) Int. Cl.
*G01F 1/10* (2006.01)
*G01F 1/12* (2006.01)
*A61B 5/00* (2006.01)

(52) U.S. Cl.
CPC .......... *A61B 5/4848* (2013.01); *A61B 5/7246* (2013.01); *A61B 5/7282* (2013.01); *A61B 5/743* (2013.01); *A61B 5/746* (2013.01); *A61B 5/7475* (2013.01); *G01F 1/103* (2013.01); *G01F 1/125* (2013.01)

(56) References Cited

U.S. PATENT DOCUMENTS

| | | | |
|---|---|---|---|
| 5,518,002 | A | 5/1996 | Wolf et al. |
| 5,816,246 | A | 10/1998 | Mirza |
| 2002/0055857 | A1* | 5/2002 | Mault ................ G06F 19/3443 705/2 |
| 2002/0151813 | A1* | 10/2002 | Niles ................... A61B 5/0875 600/532 |
| 2003/0013946 | A1* | 1/2003 | Schau .................... A61B 5/087 600/300 |
| 2003/0098022 | A1 | 5/2003 | Nakao et al. |
| 2010/0089394 | A1* | 4/2010 | Sakurada ............... A61B 5/087 128/203.14 |
| 2010/0121211 | A1 | 5/2010 | Bryant |
| 2011/0208539 | A1* | 8/2011 | Lynn ..................... A61B 5/087 705/2 |

FOREIGN PATENT DOCUMENTS

| | | |
|---|---|---|
| EP | 0196396 | 10/1986 |
| JP | 2000298044 | 10/2000 |

OTHER PUBLICATIONS

The Written Opinion for corresponding PCT Application No. PCT/US12/63551 dated Jul. 10, 2013, 8 pages.

\* cited by examiner

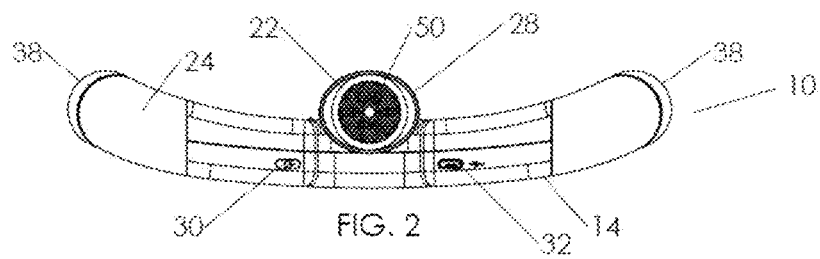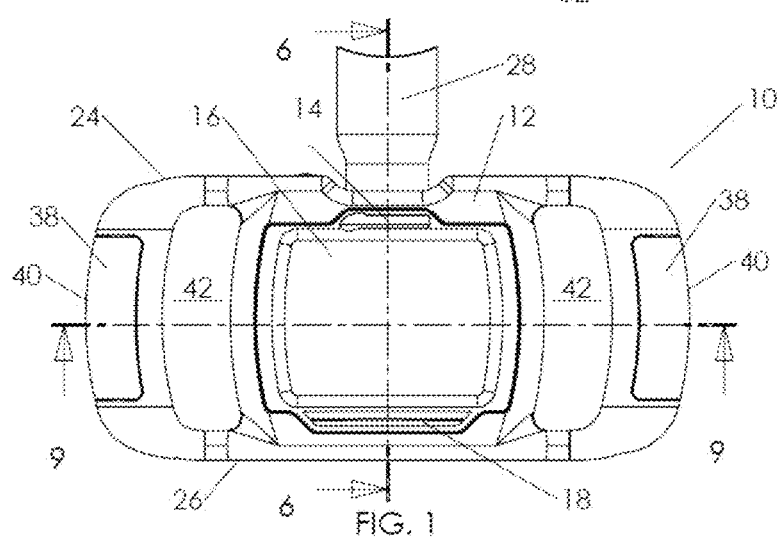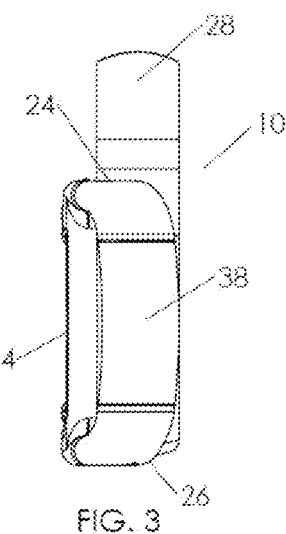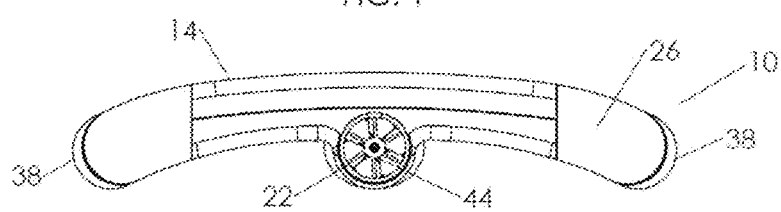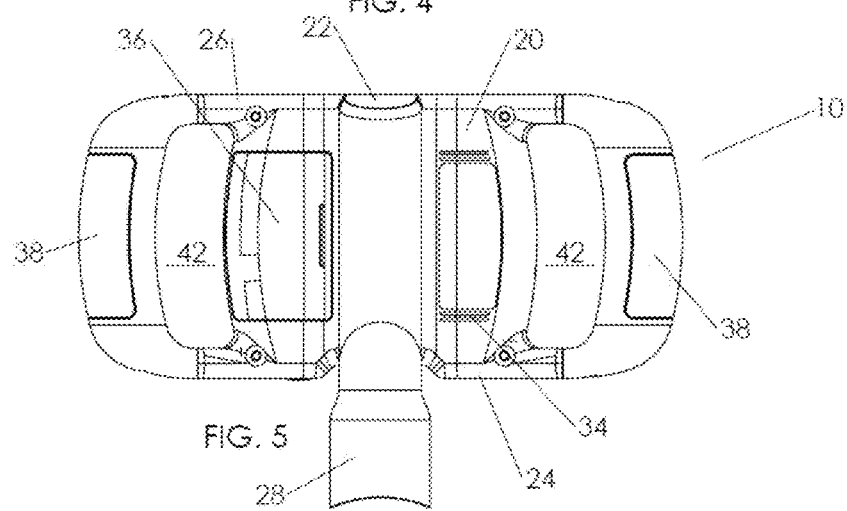

PERSONAL SPIROMETER

CROSS-REFERENCE TO RELATED APPLICATIONS

This application is the U.S. national phase application filed under 35 U.S.C. § 371 claiming benefit to International Patent Application No. PCT/US2012/063551, filed on Nov. 5, 2012, which is entitled to priority under 35 U.S.C. § 119(e) to U.S. Provisional Application No. 61/555,235, filed Nov. 3, 2011, each of which is hereby incorporated by reference in its entirety.

FIELD OF INVENTION

The invention pertains to spirometers. More particularly, The present invention relates to a spirometer or similar respiratory testing device for use in testing lung and airway capacity or function of a patient and/or for measuring the amount or volume and/or speed or flow of air that can be inhaled and/or exhaled by the patient. More particularly, the present invention relates to a portable, lightweight, hand-held spirometer particularly suitable for home and personal use, although equally capable of being used in hospitals, doctor's offices, and like institutions. The present invention is also directed to a system, software, and method for obtaining, storing, and displaying the results of spirometry tests.

BACKGROUND

In general, a spirometry test measures the air entering and leaving the lungs and airways and is often used as a preliminary test for assessing the health condition of a patient's lungs and airways as well as a means for periodically tracking the progress of disease treatment and effect of medication. The spirometry test typically is performed using a device known as a spirometer, and the data provided by the test often is provided graphically in the form of a "volume-time curve" in which volume in liters is shown along the Y-axis and time in seconds is shown along the X-axis and/or in the form of a "flow-volume loop" in which the rate of airflow is shown on the Y-axis and the total volume inspired or expired is shown on the X-axis.

By way of example, a few common parameters that may be measured during respiratory testing include: Forced Vital Capacity (FVC) which is the total volume of air that can be forcibly blown out after full inspiration; Forced Expiratory Volume (FEV) at timed intervals (for instance, at 1.0 second (FEV1)); Forced Expiratory Flow (FEF) which is the average flow (speed) of air coming out of the lungs and airways during a specified period of the expiration; and Peak Expiratory Flow (PEF) which is the maximum flow (speed) of air during maximum expiration initiated after full inspiration. These parameters often are provided in raw data form (i.e., in liters, liters/second, liters/minute, etc.) and as a percentage of a predicted value (i.e., a percent of a predicted value for a patient of similar age, height, weight, gender and ethnicity).

Each test typically is repeated three times to ensure reproducibility. The obtained results of the tests are highly dependent on patient cooperation and effort. For meaningful and valid test results to be obtained, the patient must provide vigorous and maximum respiratory effort for full expiration and/or inhalation. Typically, if the test is given during an office visit or at a hospital or the like, the patient will be coached and motivated by the attending nurse, physician, or technician to keep exhaling as hard as possible for a predetermined period of time (i.e. "keep going, don't stop"). However, no such assistance is typically provided during home use of a spirometer. Hence, the obtained home test results may not necessarily be valid if maximal effort is not provided throughout the duration of full expiration or inhalation.

SUMMARY OF INVENTION

According to one aspect of the present invention, a portable, hand-held spirometer is provided including an electronic display screen for visually presenting useful information to the user of the device. The spirometer further includes a speaker for presenting useful audible information to the user. The display screen can be a color touch screen LCD display. Thus, data entry and user control of the spirometer is provided by touching icons, test listings, or other selections displayed on the screen. In addition, a color display enables test results and graphs to be color-coded thereby permitting results considered of "high" severity to be clearly highlighted on the display.

The spirometer may include a turbine assembly within the air flow tube. The turbine assembly includes a vane mounted for spinning rotation in the air flow tube. The vane is caused to rotate by air flow through the air flow tube, and a speed of rotation of the vane corresponds to a speed of air flow through the air flow tube at any instance in time. A pair of sensor devices can be arranged on opposite sides of the air flow tube adjacent the vane. One of the pair of sensor devices is a transmitter for directing a beam of electromagnetic radiation transversely across and through the air flow tube such that the beam is interruptible by rotation of the vane. The opposed sensor device is a receiver for detecting whether or not the beam passes by the vane or is interrupted by the spinning vane at any point in time. The receiver generates and outputs an electronic digital signal to a microprocessor, and the signal corresponds to when the beam was received and when the beam was interrupted throughout duration of a respiratory test. In order to determine speed of rotation of the turbine, from which the air flow rate and volume through the turbine may be calculated, an accumulator is triggered to start counting oscillator pulses when the beam is not detected at the receiver due to interruption by a vane and to stop counting when the beam is detected at the receiver. The count is indicative of the speed of rotation of the vane, which, in turn, is converted into an airflow rate. The rate of airflow can further be integrated to determine the area under the rate curve to calculate total volume in order to generate the relevant pulmonary function of the user.

In one embodiment, the processor uses unique algorithms to compensate for inertia of the turbine, temperature, and humidity to provide more accurate test results.

In one embodiment, the microcontroller unit automatically causes the spirometer to issue alarms to remind the user of scheduled respiratory tests and times to take medication. These alarms can include both visual displays on the touch screen and audible sounds. According to other aspects of the invention, various methods of gathering, correlating, displaying and audibly presenting information on a portable, hand-held spirometer that are particularly user-friendly are provided, including, for instance, (1) medication, test, and other event reminders with a snooze function using an algorithm that balances the need to conserve battery power with the need to assure that the user is informed of such events, (2) correlating test result data, medication schedule data, medical diary data to demonstrate the effectiveness of medications, or predict medical events such as an asthma attack, and (3) providing convenient and user-friendly graphical user interfaces for various tasks, including retrieving schedule information from the device, guiding and coaching the user through test procedures, entering data, color coding data for clarity.

Other aspects of the invention include a modular design with a central processing module to which various test modules (spirometry, blood glucose metering, blood pressure metering) can be wirelessly coupled to communicate so that a user can purchase one central processing unit that can be used in connection with multiple test modules, thus reducing overall cost. In addition, the central module can communicate via wire or wirelessly with a home network and/or the internet to upload test and other data to a home computer or the internet. Such communication of data through the web can be used to provide better collection of statistics for purposes of diagnosis, adding a gaming aspect to the use of the devices, sharing of information with caregivers or members of a support group.

The device may further be coupled via wire or wirelessly to control the dosage of another, medication dosing device or to a lab-on-a-chip device for processing of the test data generated on the lab-on-a-chip, communicating the test results to caregivers, etc.

Additionally, the device may store or, alternately, access via the internet educational or exercise information that can be presented to the user of the device visually and/or audibly using the display screen and/or speaker, including textual and multimedia content.

In one embodiment, the invention involves a method for compensating for turbine inertia in a spirometer comprising a turbine, and comprises: (a) recording the speed of rotation of the turbine; (b) determining residual speed of rotation after a user stops inhaling/exhaling; and (c) calculating an airflow rate based on the speed taking into account the residual speed.

In another embodiment, the invention involves a spirometer comprising: (a) a turbine; (b) a processor; and (c) memory configured with instructions for instructing the processor to perform the following steps: (i) recording the speed of rotation of the turbine; (ii) determining residual speed of rotation after a user stops inhaling/exhaling; (iii) calculating an airflow rate based on the speed taking into account the residual speed.

In still another embodiment, the invention comprises a graphical user interface (GUI) for causing the display on a spirometer, the GUI being configured to perform the following steps: (a) generating a display having a home screen showing primary objects corresponding to different modes of operation of the spirometer, the primary objects corresponding to at least one of a run object corresponding to running a test, a data object corresponding to displaying results of one or more tests, a medical management object corresponding to managing medication, and an alarm object corresponding to setting alarms; (b) receiving a selection of a primary object; and (c) displaying a primary object screen corresponding to the primary object. In a particular embodiment, the GUI further comprising displaying a pop-up screen indicating an alarm when the user's performance is a certain amount below a baseline performance provided by a healthcare provider for the user. In one embodiment, the warning comprises a warning to seek medical attention or take medication.

In another embodiment, invention comprises a spirometer for correlating test results with a medical condition, the spirometer comprising: (a) a processor; (b) memory operatively connected to the processor and configured with instruction to instruct the processor to perform the following steps: (i) recording spirometer results of a user; (ii) correlating the results with user data, the user data comprising at least one of a medication log, a medical diary, a baseline performance for the user provided by a healthcare provider, or other results from other testing devices; and (iii) indicating a relationship between the results and the user data. In a particular embodiment, the indication includes a warning to seek medical attention immediately or to take medication.

Yet another embodiment involves a method of motivating a user to optimize performance on a spirometer, the method comprising: (a) instructing the user to inhale/exhale into the spirometer; (b) measuring the inhalation/exhalation; (c) determining if user's performance meets predicted performance; and (d) if the user's performance does not meet predicted performance, recommending a specific change in the user's performance to meet the predicted performance.

Still another embodiment is a controller for managing data from one or more medical devices, the controller comprising: (a) a first interface to one or more of the medical devices; (b) a database for storing test results and event information from the medical devices; (c) a user interface for communicating with a user; (d) a second interface for connecting to a healthcare service and providing at least a portion of the test results or event information to the healthcare service; (e) a processor; and (f) memory operatively connected to the processor and configured for instructing the processor to perform the following steps: (i) periodically transmitting information based on the test results or the event information to the healthcare service over the second interference.

BRIEF DESCRIPTION OF DRAWINGS

FIG. 1 is a plan view showing a front panel of a spirometer according to the present invention.

FIG. 2 is an elevational view of a proximal, top, mouth-piece end of the spirometer of FIG. 1.

FIG. 3 is a side elevational view of the spirometer of FIG. 1.

FIG. 4 is an elevational view of a distal, bottom end of the spirometer of FIG. 1 opposite the mouth-piece end.

FIG. 5 is a view of the rear panel of the spirometer of FIG. 1 opposite the front panel.

DETAILED DESCRIPTION

Figure 6:
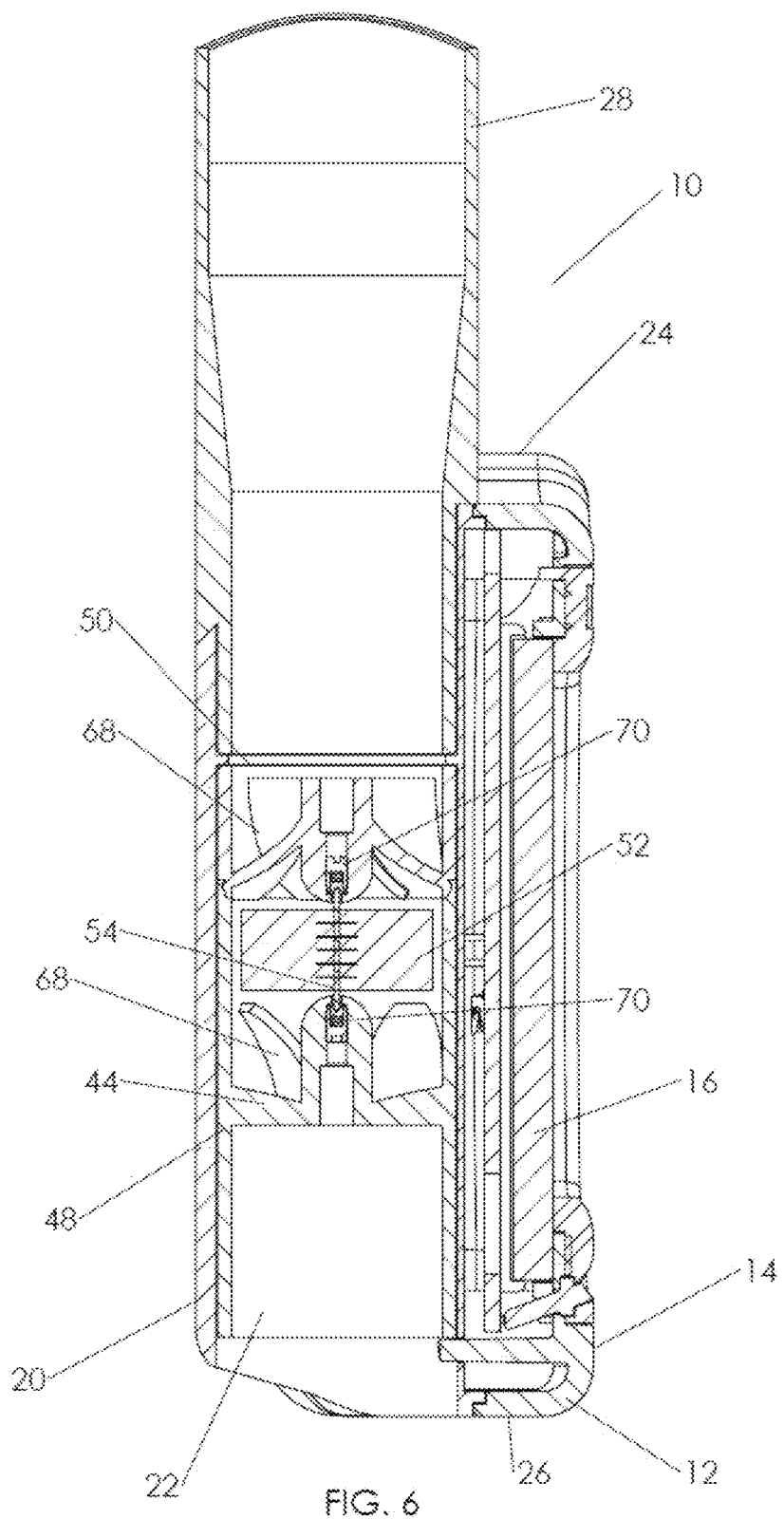
FIG. 6 is a cross-sectional view along line 6-6 of FIG. 1.

U.S. patent application Ser. No. 12/844,980 filed on Jul. 28, 2010, incorporated herein fully by reference, and owned by the same assignee as the present application, discloses a personal spirometer adapted primarily for home use.

The basic exterior structure of a spirometer 10 according to the present invention is best illustrated in FIGS. 1-5. From the drawings, the spirometer 10 can have a relatively thin, elongate, rectangular casework or housing 12 that can be made, for instance, of plastic, metal, composite material, or the like. Of course, other shapes and materials for the casework housing 12 can be utilized. The illustrated embodiment is designed such that it is portable, lightweight, and compact and provides a hand-held, battery-powered device suitable for home or personal use, although not limited to such use. The overall size of the spirometer 10 is such that it can be readily stored in a handbag, drawer, or the like and/or can be carried and taken with the patient as needed.

The front panel 14 of the spirometer includes a display screen 16 and can also have a coaching mechanism/indicator 18, and the rear panel 20 defines the location of an air flow tube 22 that extends at a central location across the spirometer 10 from a proximal top end 24 to a distal bottom end 26. A mouthpiece 28 is located on the end of the air flow tube 22 and extends forward of the proximal top end 24 of the spirometer 10. The mouthpiece 28 can be made of transparent material for ease of cleaning and have an ergonomic design that provides comfort during use. The spirometer 10 can also include a power button 30 and a connection port 32, such as a micro USB port, on the proximal top end 22 and a speaker/grill 34 and removable battery compartment panel door 36 on the rear panel 20. The batteries (not shown) can be rechargeable, and the spirometer 10 can also be powered via use of an AC power adaptor.

The casework housing 12 includes a pair of oppositely located handgrips 38 that extend on opposite sides 40 of the spirometer 10 and that form the side edges of the spirometer 10. In addition, the casework housing 12 includes a finger-receiving through hole 42 adjacent each handgrip 34. Each through hole 42 permits the fingers of the person gripping the spirometer 10 to extend completely around the handgrips 38 such that each handgrip 38 can be tightly gripped and squeezed in the hand of the user. As best illustrated in FIG. 5, each handgrip 38 is generally elongate and extends substantially along and in the same direction/orientation as the air flow tube 22, and each handgrip 38 can be equally spaced from the centrally located air flow tube 22. Also, as best illustrated in FIG. 3, the central longitudinally-extending axis of each of the handgrips 38 and the central longitudinally-extending axis of the air flow tube 22 are essentially aligned and coplanar (i.e., extend substantially within the same imaginary plane). According to one embodiment, the outer surface layer of each handgrip 38 is textured to provide a non-slip surface and is made of rubber, an elastomeric material, or the like that is at least slightly deformable and elastic such that the handgrips 38 can be squeezed in the grip of the user.

Figure 18:
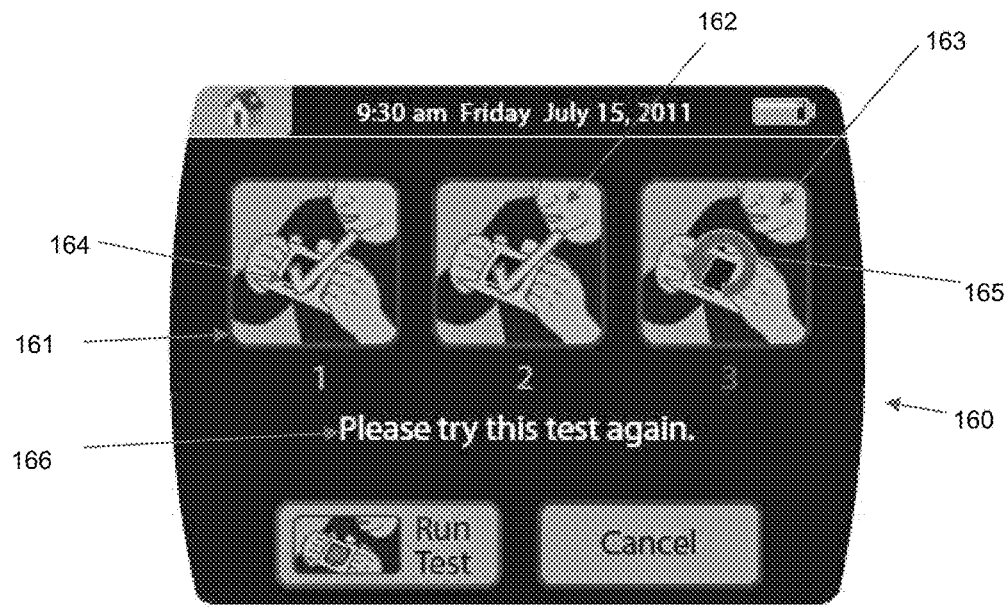
FIG. 18 is a screen shot image provided by the display screen of the spirometer providing further visual instructions with respect to using the device for a lung function test run.

The configuration of the handgrips 38 of the spirometer 10 provides an important function in properly positioning the user to ensure maximum respiratory effort and results during a respiratory test. In use, preferably the user sits or stands with their back in a generally upright position and with shoulders arched backward (i.e., not in a slumped forward position) with good posture. The user grips the spirometer 10 tightly with both hands as best illustrated in FIG. 18. Thus, one hand of the user grips one of the handgrips 38 with the fingers of the user extending completely through the adjacent through hole 42 such that user's hand completely encircles and girds the handgrip 38, and the other hand of the user grips the other handgrip 38 with the fingers of the user extending completely through the adjacent through hole 36 such that user's hand completely encircles and girds the handgrip 38. In this position, the shoulders of the user are flexed backward and the arms of the user extend laterally and generally horizontally with bent elbows of the user pointing laterally and outward. In this balanced and proper posture position, the chest of the user is generally "open" and ready for maximum inhalation and/or exhalation.

Thus, for example, the user takes a deep breath while in the above described position, places his/her mouth about the mouthpiece 28, and exhales into the air flow tube 22 of the spirometer 10 as hard as possible for as long as possible to generate meaningful and valid test results which are measured and stored by the spirometer 10.

Another aspect of the spirometer 10 is that it includes a mechanism that provides real-time, automatic coaching and assistance to the user with respect to the expected duration of full expiration and/or inhalation. Thus, this mechanism provides a further means to ensure that the best possible test results are obtained by providing meaningful information to the user in real-time, for instance, while the user is exhaling into the spirometer 10 during a test. More specifically, the spirometer 10 includes the coaching mechanism/indicator 18 on the front panel 14 which is in full view by the user as the user is exhaling into the spirometer 10 or inhaling through the spirometer 10.

According to one embodiment, the indicator 18 is in the form of an elongate continuous or discontinuous line or sequence of light such as provided, for instance, by a light pipe, a series or array of light-emitting diodes (LEDs), or like visual indicator. Other visual effects also can be used, such as images or the like, and the display screen 16 can be used for this purpose. An audible indicator (such as sounds emitted from the speaker/grill 34) can be used simultaneously in conjunction with the coaching indicator 18 or in place of the coaching indicator 18 for providing the same general purpose.

The coaching indicator 18 can be specifically used to reflect the expected Force Vital Capacity (FVC) or other measurements (i.e., the total volume of air that can be forcibly blown out after full inspiration) of the patient or the expected Inspiratory Vital Capacity (IVC) (i.e., the total volume of air that can be inhaled after full exhalation). For instance, the user's age, height, weight, gender, and ethnicity are entered into the spirometer 10 via use of the display screen 16, which for example can be a color touch-screen LCD display, and these entries can be stored in a microprocessor and/or other electronic memory provided within the spirometer 10. Alternatively, these data entries can be input into the spirometer 10 via an external computer connected to the spirometer 10 via the connection port 32, which can be a micro USB port. From this information, the microprocessor of the spirometer 10 calculates a Predicted Force Vital Capacity (PFVC) and/or a Predicted Inspiratory Vital Capacity (PIVC) expected for a person of the age, height, weight, gender and ethnicity entered and sets this as the value required to fully light the coaching indicator 18, thereby providing an indication to the user in real-time of the duration of exhalation or inhalation sufficient to generate valid test results.

Figure 7:
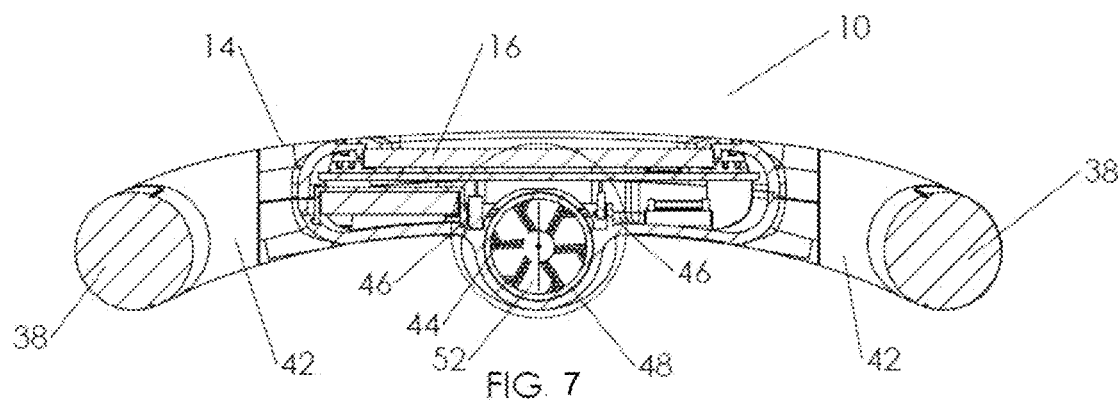
FIG. 7 is a cross-sectional view along line 7-7 of FIG. 1.
Figure 8:
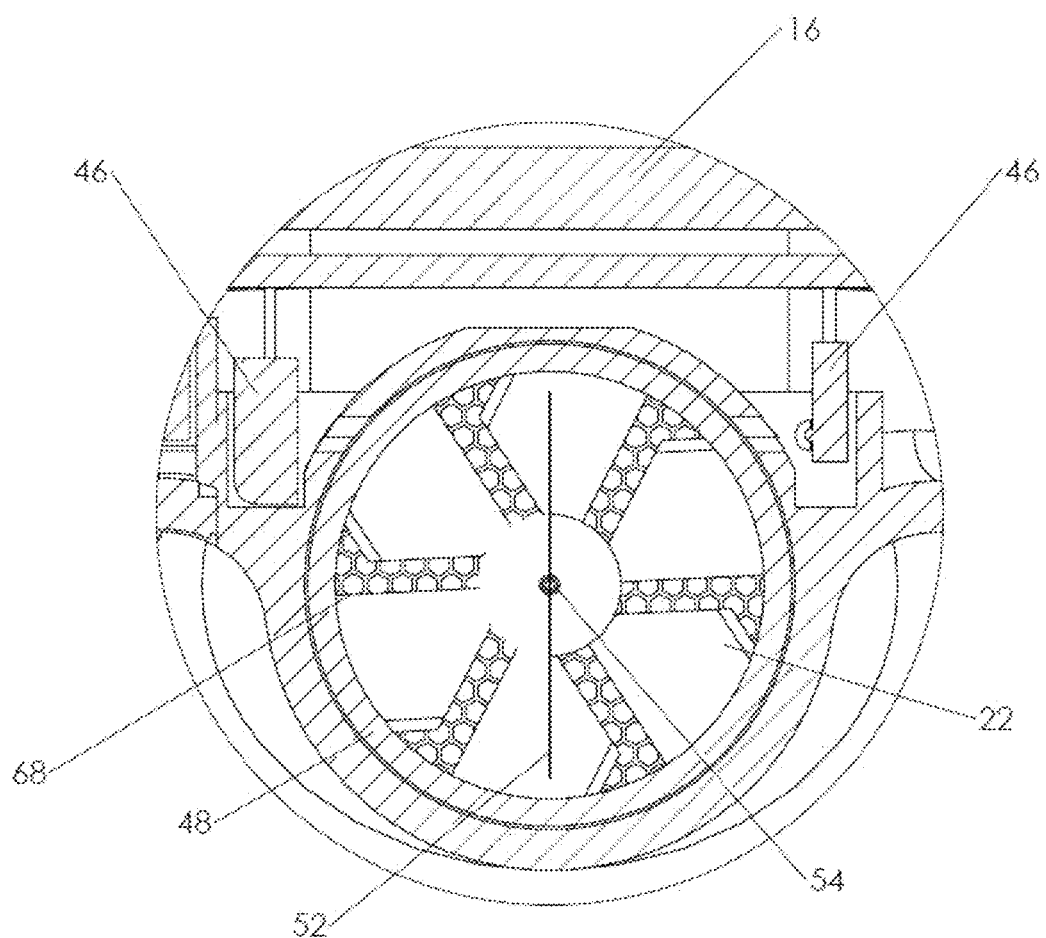
FIG. 8 is a magnified view showing a pair of turbine rotation sensors that detect rotation of a rotor within an air flow tube of the spirometer of FIG. 1.
Figure 9:
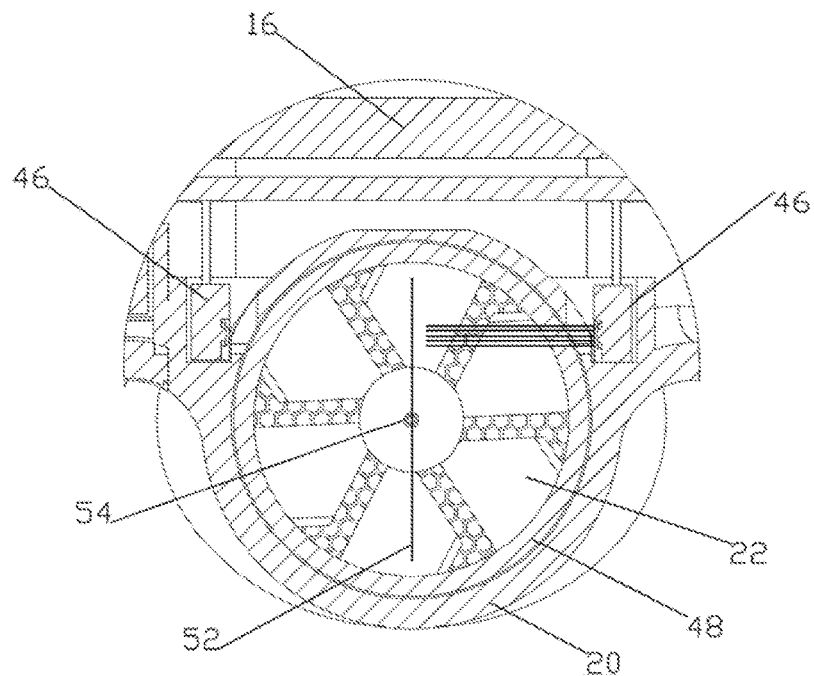
FIG. 9 is a view showing the pair of turbine rotation sensors of FIG. 8 in which a vane of the rotor blocks a beam of electromagnetic radiation, such as a beam of infrared radiation, from being received by a receiving sensor.

In use, before a user exhales (or inhales) into the spirometer 10, the elongate visual indicator 18 is completely unlit or "off" as best illustrated in FIG. 7. However, as the user begins exhaling (or inhaling) into the air flow tube 22 of the spirometer 10, the total volume of air flowing through the tube is continuously measured in real-time during the test, and the proportion of the Predicted Force Vital Capacity (or Predicted Inspiratory Vital Capacity) measured based on the real-time calculation is determined and reflected by the extent to which the coaching indicator 18 is lit or "on". Thus, one end of the visual indicator 18 will become lit, and as the user continues to exhale (or inhale) into the spirometer 10, progressively more of the visual indicator 18 will light-up as best shown in FIG. 8, until the entire indicator 18 is lit or "on". In this manner, the indicator 18 coaches and provides incentive to the user to continue to exhale (or inhale) into the air flow tube 22 at least until the full length or a predetermined length of the visual indicator 18 is lit which reflects the predicted volume of air expected during full exhalation (or full inhalation) by the particular patient. Thus, the patient is coached to "don't stop, keep going" by the coaching mechanism 18 and the user can view the indicator 18 during a test so that meaningful and reproducible results can be obtained.

In another embodiment, incentive to exhale or inhale is provided by a virtual incentive spirometer shown in the graphical user interface. Incentive spirometers are conventionally mechanical devices given to users to exercise their lungs. It comprises a ball in a gradated tube. By inhaling/exhausting through the device, the ball floats with in the tube—the higher the tube floats, the greater the air flow. For exercise, users are instructed to exhale/inhale to float and hold the ball at a certain level. The home spirometer device of the present invention combines the incentive spirometer and traditional spirometer in one, which is unique because neither incentive spirometer (which is available in mechanical form) nor an office spirometer (which is not a personal device) can combine these two totally different applications together.

According to one embodiment as best illustrated in FIG. 6, the spirometer 10 of the present invention measures the flow of air through the air flow tube 22 with a turbine assembly 44 and at least one pair of oppositely located rotation-detecting sensor devices 46.

The air flow tube 22 generally includes the mouthpiece 28 and a turbine tube 48 which are connected end-to-end by the housing 12 with a mesh protective screen 50 or the like provided therebetween. The mesh screen 50 prevents foreign objects from entering and possibly damaging the turbine assembly. The mouthpiece 28 can be removable from the spirometer 10 for cleaning and/or replacement purposes.

A vane 52 is mounted for rotation on a spindle 54 within the turbine tube 48 between a series of stationary air flow deflectors 68. The opposite ends of the spindle 54 are positioned and ride within vee jewel assemblies 70 that enable the spindle 54 to rotate about its longitudinal axis within the turbine tube 48. The vee jewel assemblies 70 are high precision spring-loaded bushings that greatly reduce friction thereby permitting high revolutions per minute (RPMs) to be achieved by the vane 52 and spindle 54. Thus, when the user exhales (expires) or inhales (inspires) into/out of the air flow tube 22, the flow of air through the turbine tube 48 will cause the vane 52 and spindle 54 to rotate. The vane 52 will rotate faster when the speed of the air flow is greater, and the vane 52 will rotate slower when the speed of air flow decreases. In addition, the direction of rotation of the vane 52 and spindle 54 can be monitored to determine whether the patient is exhaling or inhaling into the spirometer 10.

The rotation of the vane 52 is monitored by the rotation-detecting sensor devices 46 mounted in opposite positions relative to the turbine tube 48. The sensor devices 46 are best illustrated in FIGS. 7-10. One of the sensor devices 46 can include a transmitter for transmitting a beam of visible or invisible light or electromagnetic radiation and the other sensor device can include a receiver for receiving/detecting the presence or absence of the beam at the receiver location. By way of example, the sensor devices 46 can include a diode for emitting a beam of infrared radiation or light (invisible to the human eye) and a photo-transistor that detects the presence or absence of the infrared light beam.

Figure 10:
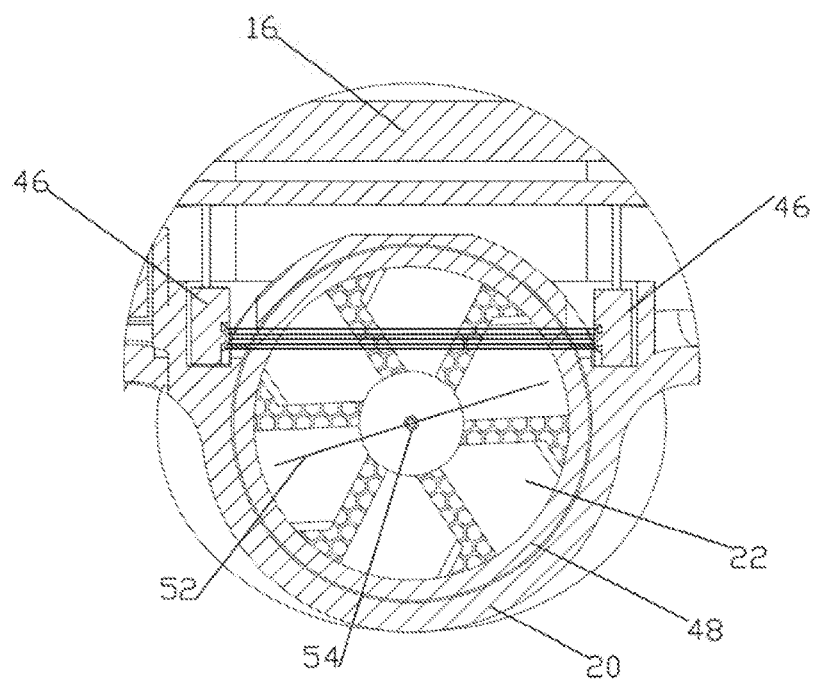
FIG. 10 is a view showing the pair of turbine rotation sensors of FIG. 8 in which the beam of electromagnetic radiation, such as a beam of infrared radiation, passes by the vane of the rotor and is received by the receiving sensor.

As best illustrated in FIG. 10, the sensor devices 46 can be mounted at opposite positions about the turbine tube 48. In this position, a beam of infrared radiation or light, or other beam of electromagnetic radiation, can be emitted transversely across and within the tube at the location of vane 52. In this manner, rotation of the vane 52 can interrupt the beam (see FIG. 9) or permit the beam to pass (see FIG. 10) depending upon the relative angular position of the rotating vane 52 at any instance of time.

The flow can be measured on a timed basis, and the microprocessor can convert this information to an accumulated volume based on well-known formulae programmed into the microcontroller firmware. For example, when the patient is exhaling into the spirometer 10, the accumulated volume measurement is equivalent to a measurement of Forced Vital Capacity (FVC), or when the patient is inhaling through the spirometer 10, the accumulated volume measurement is equivalent to a measurement of Inspiratory Vital Capacity (IVC).

The speed of rotation of the turbine can be converted directly into an air flow rate with relatively high accuracy, although the inertia of the turbine can introduce small error, particularly towards the end of an exhalation when the air flow rate is low and decreasing relatively slowly while the turbine is still rotating faster than would be dictated by the air flow rate due to inertia from having recently been spinning much faster. There also is an inertia error when the user first starts exhaling in that the stationary turbine must overcome its inertia of non-movement to catch up to the airflow. However, since the beginning of the breath commonly is very powerful, such that the turbine catches up to the airflow rather quickly and the inertia error is usually small enough to be neglected. However, at the end of the breath, when airflow is very low, the inertia of the quickly spinning turbine introduces a still small, but more significant error.

Integrating the air flow rate over time provides the volume of the air exhaled (or inhaled, if an inhalation test). Thus, the speed of the turbine is determined in accordance with one aspect of the invention by determining the duration for which each vane of the turbine interrupts the beam between the transmitter and the receiver, which is directly convertible into a rotation speed of the turbine, and which, in turn, is convertible into an air flow velocity through the turbine. Of course, it should be understood, that, alternately, one could measure the period during which the beam is not interrupted or even the entire duty cycle between interruptions to obtain the same data.

Figure 11:
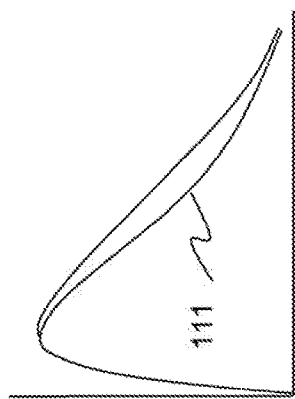
FIG. 11 is a graph showing an exemplary air flow graph for an FVC lung function test.

The shorter the interruption (hereinafter "interruption pulse"), the faster the turbine is spinning, and, thus, the higher the air flow rate. Thus, the duration of the interruption pulse is directly convertible into an airflow rate by multiplying the inverse of the duration (i.e., 1/X, where X is the duration) by an appropriate conversion factor, Y. FIG. 11 is a graph in which line 111 shows a flow rate as a function of time for a typical FVC test. Particularly, the flow rate increases rapidly from zero when the person starts to exhale as rapidly as possible, reaches a peak flow rate that lasts for a relatively short period of time, and then is followed by a more gradual decrease in flow rate as the person runs out of air in his or her lungs. Line 113 illustrates the inertia error discussed above. Specifically, as noted, the inertia of the turbine will cause the turbine to rotate slightly faster than would be dictated by the actual flow rate of air within the breathing tube as the user is slowly decreasing the exhalation flow rate. The difference between liens 111 and 113 is the error due to inertia.

Figure 12:
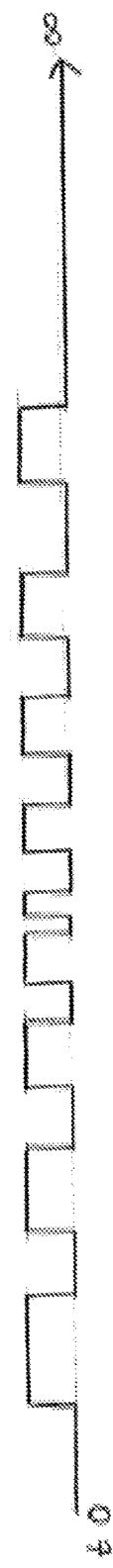
FIG. 12 is a pulse diagram showing one form of turbine speed data in accordance with the principles of the invention.

In any event, FIG. 12 shows an interruption pulse train illustrative of the FVC test results shown in FIG. 11, where the flow rate increases rapidly at the start, reaches a peak rate and then decreases more gradually than it initially rose duration of the high part of the pulse corresponds to interruption of the beam. Specifically, the duration of each pulse is inversely proportional to the speed of rotation of the turbine during the duration of that pulse. Thus, as can be seen in FIG. 12, the pulses start out relatively short and become shorter initially because the turbine speeds up rather quickly under the strong initial force of exhalation, and then the pulses become longer and longer more gradually as the air flow rate decreases gradually. Note that when the turbine stops, the last pulse is infinite because, with the turbine stopped, the beam is either interrupted or not (either is possible) but does not change if the turbine is not rotating.

Figure 13:
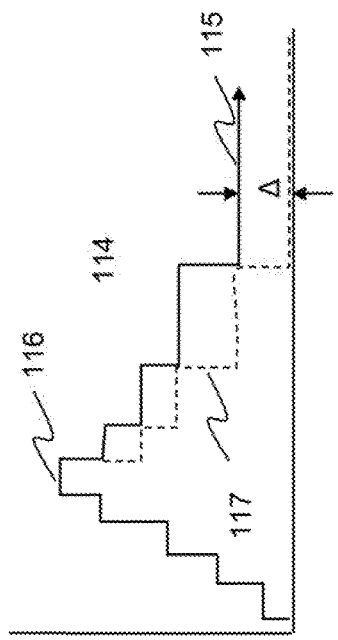
FIG. 13 is a diagram showing pulse data such as is illustrated in Figure converted into an airflow rate graph.

In one embodiment, the pulse duration data is collected by free running a 1.5 MHz counter and counting the duration of interruption (or alternately, non-interruption or alternately, the entire duty cycle between corresponding edges, whether rising or falling). In accordance with one embodiment of the invention, a rising edge on the pulse signal line signifies that the beam has been interrupted and a falling edge signifies that the beam has returned. Thus a rising edge is used to reset the counter to zero and continues to count until reset again by a next rising edge of the turbine signal. To determine the end of the pulse, a falling edge on the pulse signal line causes the count of the counter at that instance to be recorded. This occurs continuously until the turbine stops spinning (or for a predetermined period, for example, until 20 seconds have passed since the first rising edge if the turbine is still spinning). The duration of each pulse in a test set is converted into an air flow rate. Thus, in essence, every complete duty cycle of the pulse train (i.e., rising edge, followed by high level, followed by falling edge, followed by low level until the next rising edge is detected) corresponds to one airflow rate data point. In one embodiment, a smooth FVC curve can be constructed from these data points by interpolating between them. However, in another embodiment such as illustrated in FIG. 13, the data points can be used to build a graph of the air flow rate that is a step function 114, wherein each step corresponds to the air flow rate value of an interruption pulse, which level is maintained until the start of the next pulse. As can be seen, the steps are much shorter in time duration when the turbine is spinning more quickly and are longer in duration when the turbine is spinning more slowly. When the turbine eventually stops so that the light beam is either permanently interrupted (or uninterrupted), that last step is infinite and, therefore, does not get recorded or used. Thus, the step wave form never goes down to zero, but stops at the level corresponding to the last full duty cycle of the sensor signal.

The fact that the last data point/step never gets to zero is actually advantageous because it can be used to compensate for the aforementioned inertia error. The system compensates for the inertia of the turbine during the period when the air flow is decreasing gradually (near the end of the breath) by resetting the value of the last step 115 to zero and subtracting the original last step value from each preceding step until (but excluding) the highest air flow rate step 116. This is illustrated by the dashed line 117 in FIG. 13. It has been found that this adjustment substantially corrects for the inertia error that would otherwise exist in the data.

Figure 14:
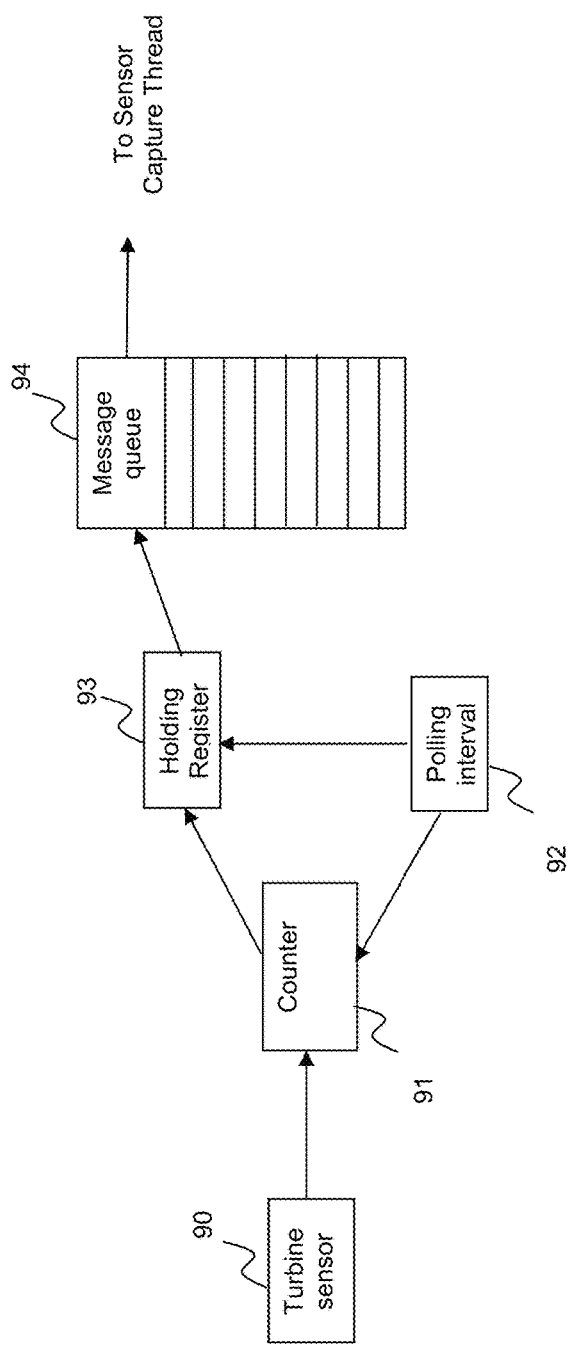
FIG. 14 is a block diagram illustrating the components involved in turbine data collection in accordance with the principles of the invention.

FIG. 14 is a block diagram illustrating one embodiment of componentry for recording the pulse durations. The turbine signal 90 (i.e., the pulse train corresponding to the interruption and non-interruption of the beam) is fed to a 1.5 megahertz free-running, sixteen bit counter 91. A rising edge in the turbine signal 90 resets the counter 91 to zero and a falling edge on the turbine signal 90 causes the counter value at the falling edge to be saved. The counter 91 writes its count data to a sixteen bit Holding Register 93. A polling interrupt signal 92 is generated, for example, every 10 ms, which causes the counter 91 to take some actions, such as writing a count to the Holding register, resetting the count to zero, setting or resetting a Carry Flag, etc. The particular actions at any given polling instance will depend upon the condition of various signals in the system, as will be described in greater detail below. Also, the polling signal 92 always causes the Holding Register 93 to write its contents (the count) to a Message Queue 94. The Message Queue stores all the count data consecutively.

When all of the count data for a particular lung function test has been captured and stored in the Message Queue 94, a sensor capture software thread can then process the count data to convert the count data into a series of actual airflow values from which a graph of the data may be generated. It should be noted that, when the turbine is spinning very fast, it is possible that multiple pulses can occur within a single 10 ms polling interval, and when the turbine is spinning slowly, a single pulse may last for several 10 ms intervals. Thus, the sensor capture thread 95 must analyze the data in the Message Queue 94 to determine such things as when consecutive values stored in the Message Queue 94 need to be summed with each other in order to derive a complete pulse duration and which do not. The sensor capture thread also converts the pulse duration data into air flow rate data and also may correct for turbine inertia at the end of the exhalation, as described above, and/or compensate for temperature and/or humidity differences, also as described above.

Below is a table disclosing the operation of the hardware shown in FIG. 14 for determining and storing the lengths of the interruption pulses in accordance with one embodiment of the invention.

Note the following explanatory notes for the table below. In the table, the Interruption Pulse signal is the output of the sensor indicating whether the beam is interrupted (a high level or "pulse") or uninterrupted (a low level). As will become clear below, at the end of each polling interval, the Carry Flag is set if the sensor signal is active, indicating that a pulse is ongoing at the end of the interval and continues into the next interval, and is reset otherwise.

The Carry Flag is a flag inside of the counter and is written to the holding register and Message Queue along with the count. It is this Carry Flag that the Sensor Capture Thread will use to determine whether or not it needs to sum consecutive counts stored on the Message Queue to derive the entire duration of a pulse. In fact, since a 1.5 MHz counter can count up to a maximum of 15,000 in a 10 ms interval, only 14 bits of count data can exist at any time. This leaves two extra bits in the sixteen bit Counter 91 and Holding Register 93, one of which bits can be used as the Carry Flag separately from the count.

The Falling Edge Detected column in the table refers to whether a falling edge occurred, for example, during the preceding 10 ms polling interval, which would indicate that the interrupted light beam became uninterrupted during the preceding polling interval. It should be noted that, in fact, the beam can become uninterrupted more than once within a polling interval, but if it happens at least once, the Falling Edge Detected bit will become set. On a rising edge of the interruption pulse, the hardware always resets the counter to zero and, on a falling edge, the hardware always stores the count at the instance of the falling edge into the Holding Register.

The only task performed by software in the counting portion of FIG. 14 (everything other than the Sensor Capture Thread 95) is, when there is more than one falling edge between consecutive polling intervals (e.g., at least one entire duty cycle occurs within one 10 ms interval), it stores the count at the first falling edge and the count at the last falling edge within the interval. Any additional falling edges are ignored and it is assumed that the duration of any of the ignored pulses within the interval had the same duration as the last pulse within the interval, which is a reasonably safe assumption when pulses are short enough for multiple pulses to occur within one 10 ms polling interval (i.e., the turbine is spinning very fast).

Finally, it should be noted that, inherently, in the system as described herein, at each polling instance, the contents of the Holding register which are written to the message queue reflect the count data collected during the preceding polling interval, not the current polling interval.

| | Conditions at polling instance | | |
|---|---|---|---|
| Interruption Pulse | Carry Flag | Falling edge detected | Actions |
| 0 | 0 | 0 | Explanation |
| | | | This set of conditions means that the beam was uninterrupted for the entire duration of the interval, and thus, the count will be zero and need not be written into the Holding Register |
| | | | Actions |
| | | | Write contents of Holding Register to Message Queue (recall that the value in the Holding Register is always the count from the previous polling interval) |
| 0 | 0 | 1 | Explanation |
| | | | This set of conditions means that a pulse started and ended during the preceding 10 ms and another one did not start. Specifically: (1) the fact that the interruption pulse is low means that the beam was uninterrupted at the end of the interval; (2) the fact that the Carry Flag is low means that the beam was uninterrupted at the end of the preceding interval; and (3) the fact that the Falling Edge Detected bit is set means that the beam had been interrupted at some point during the interval. Hence, a rising edge also must have occurred during this interval such that the count that is written into the Holding Register is the duration of one entire pulse that occurred entirely within this interval. In fact, more than one pulse may have occurred in this interval, but the duration of only the last one will be recorded |
| | | | Actions |
| | | | Write contents of Holding Register to Message Queue<br>Write the count when the first latched falling edge occurred to the Holding Register |
| 0 | 1 | 0 | Explanation |
| | | | This set of conditions means that the beam was uninterrupted for the entire duration of the interval. However, the Carry Flag is set as a remnant of the preceding 10 ms polling interval. Thus, there is no information to record for this interval and the Carry Flag should be reset |

-continued

| Conditions at polling instance | | | |
|---|---|---|---|
| Interruption Pulse | Carry Flag | Falling edge detected | Actions |
| | | | Actions |
| 0 | 1 | 1 | Clear Carry Flag<br>Write contents of Holding Register to Message Queue<br>Place a zero in the Holding Register<br>Explanation |
| | | | This set of conditions means that a pulse ended during the 10 ms interval (because a falling edge was detected) and that this pulse had started in a preceding 10 ms interval (because the Carry Flag is set) and, thus, the count at the first falling edge must be summed with the previous count that was written to the Holding Register to produce the full length of the pulse. (Note that another pulse may or may not have started during this 10 ms interval. Software independently makes that determination)<br>Actions |
| 1 | 0 | X | Clear Carry Flag<br>Add first latched falling edge count to count already in Holding Register<br>Then write the contents of Holding Register to Message Queue<br>If second falling edge occurred (which would mean that after the one pulse ended, an entire second pulse occurred during the same 10 ms interval)<br>Write the second latched falling edge count into Holding Register<br>else (which would mean that no part of any other pulse exists in this 10 ms interval)<br>Write a zero into Holding Register<br>Explanation |
| | | | This set of conditions means that at least one pulse started during this 10 ms interval (because the beam is interrupted at the end of the interval, but there was no Carry Flag from the previous interval) and that a pulse is ongoing at the end of the interval. Since, as previously indicated, if an entire pulse has occurred within a single polling interval and another pulse has at least started, the turbine is spinning very fast, such that any difference in lengths between the pulse or pulses that occurred entirely within the interval and the next pulse is/are negligible. Hence, we simply assume that all of those pulses had the same duration as the last pulse that started in that polling interval. Thus, even if there were intermediate pulses within the interval (as indicated by the falling edge flag being set), we will not record the duration of those intermediate pulses. Thus, we do not process the data any differently if a falling edge was or was not detected during the interval.<br>Actions |
| 1 | 1 | 0 | Write contents of Holding Register into Message Queue<br>Set Carry Flag<br>Write count to Holding Register<br>Explanation |
| | | | This set of conditions means that a pulse that had started in a previous interval (this is known because the Carry flag is set) continued for the entire duration of this 10 ms interval (this is known because the beam is still interrupted at the end of the interval and there was no falling edge during the interval)<br>Actions |
| | | | Write contents of Holding Register to Message Queue<br>Set Carry Flag<br>Write current count to Holding Register |

-continued

Conditions at polling instance

| Interruption Pulse | Carry Flag | Falling edge detected | Actions |
|---|---|---|---|
| 1 | 1 | 1 | Explanation |
| | | | (This set of conditions means that at least one pulse ended in this 10 ms interval, at least one new pulse started, and the last pulse that started in this interval Is still ongoing at the end of the interval) |
| | | | Actions |
| | | | |
| | | | Clear Carry Flag |
| | | | Add count (with Carry Flag reset) at the first latched falling edge to the count already in Holding Register |
| | | | Then write contents of Holding Register into Message Queue |
| | | | Then set Carry Flag |
| | | | Write current count to Holding Register |

The operation of the spirometer 10 can be controlled by software, firmware, or the like contained within the spirometer 10 via a microprocessor, microcontroller unit, or the like. Preferably, the display screen 16 is a touch screen used to display various icons or the like that can be touched to activate a specific function. Thus, the software receives the user's inputs via the touch screen and provides an appropriate response via displaying further information on the display screen 16.

By way of example and with reference to FIG. 15, the spirometer 10 comprises a graphical user interface (GUI) configured to display a home screen 100 having a plurality of icons occupying the center of the screen, each corresponding to a set of device functions having a common theme (hereinafter "top level domain") which can include, for instance, a Run Test icon 103, a View Trends icon 105, a Manage Medicines icon 107, and a Set Alarm icon 109. Any of these icons can be touched by the user to activate the corresponding functionality of the spirometer. Display area 115 near the top of the screen displays the time, day of the week, and date. It further includes an Upload Data icon 101, which can be considered to correspond to a fifth major functionality theme.

The home screen can also include a battery icon 111 showing the status of charge of the rechargeable battery. The bottom approximate one-quarter of the home screen 100 includes a scrollable display portion 113 comprising a list of upcoming and/or past scheduled events or alarms, such as respiratory tests and medications scheduled to be taken.

The scrollable display portion 113 comprises a left arrow 115 at the left end of portion 113 and a right arrow 117 at the right end of portion 113. Between the two arrows is displayed information pertaining to medical events. In the illustrated embodiment, the data for two events appears in two screen areas 119 and 129 between the arrows 115 and 117. In one embodiment, in the default condition (e.g., upon power up of the spirometer), the scrollable portion 113 displays the most recent past event and the soonest upcoming event. An event may comprise anything for which the device is used, such as, but not limited to, spirometry tests, scheduled medications, lung exercises, or any other schedule event in the spirometer. In FIG. 15, for instance, area 119 displays the basic information for the most recently performed lung function test. Particularly, the check mark icon 121 signifies this event as a past event. Furthermore, it displays the date and time at 123. Further, it contains an abbreviated description of the event at 125. Particularly, in this example, the event was a forced vital capacity (FVC) test. Finally, portion 127 indicates the FVC value, namely, 5.2 liters.

Portion 129 of scrollable screen portion 113, displays the next future event in the schedule. More particularly, the clock icon 131 indicates that this event is a future event. In addition, the time and date of the event is displayed at 133. Finally, a brief or abbreviated description of the event is provided at 135. In this particular example, the event is a scheduled dosage of one medication.

By touching the left arrow 115, the user can scroll backwards in time one event per touch. Thus, for instance, if the user presses the left arrow 115 one time, the lung function test performed at 3:00 PM on July 14 that appears on screen area 119 in FIG. 15 would move rightward and now appear in screen portion 129, and the next most recent past event stored in the device would appear in screen portion 119. Likewise, if the user touches arrow 117, the events would scroll in the opposite direction, i.e., toward the future. By touching either screen portion 119 or 129, the user can call up a new screen displaying more detailed information about the particular event that was summarized in that screen portion. For instance, with respect to the medication dosage upcoming at 12 PM on July 15, touching screen portion 129 will cause a more detailed display screen to appear showing, for instance, the name of the medication, the dosage, and other relevant information.

Thus, scrollable screen portion 113 provides a very convenient scrollable executive summary of relevant events.

When it is time for a scheduled event or alarm, a pop-up screen automatically appears on the touch screen display 16 alerting the user of the event (e.g., run a test, take a medicine, or dismiss the event/alarm). An audible alarm may simultaneously be generated.

In accordance with other user interaction aspects of the invention, since a user of the device 10 may not be able to perform an event exactly at the time of an alarm, the device is programmed with useful snooze/delay functionality, including an algorithm that balances the potentially conflicting interests of conserving battery power in the device and assuring that the user is made aware of the events.

Figure 15:
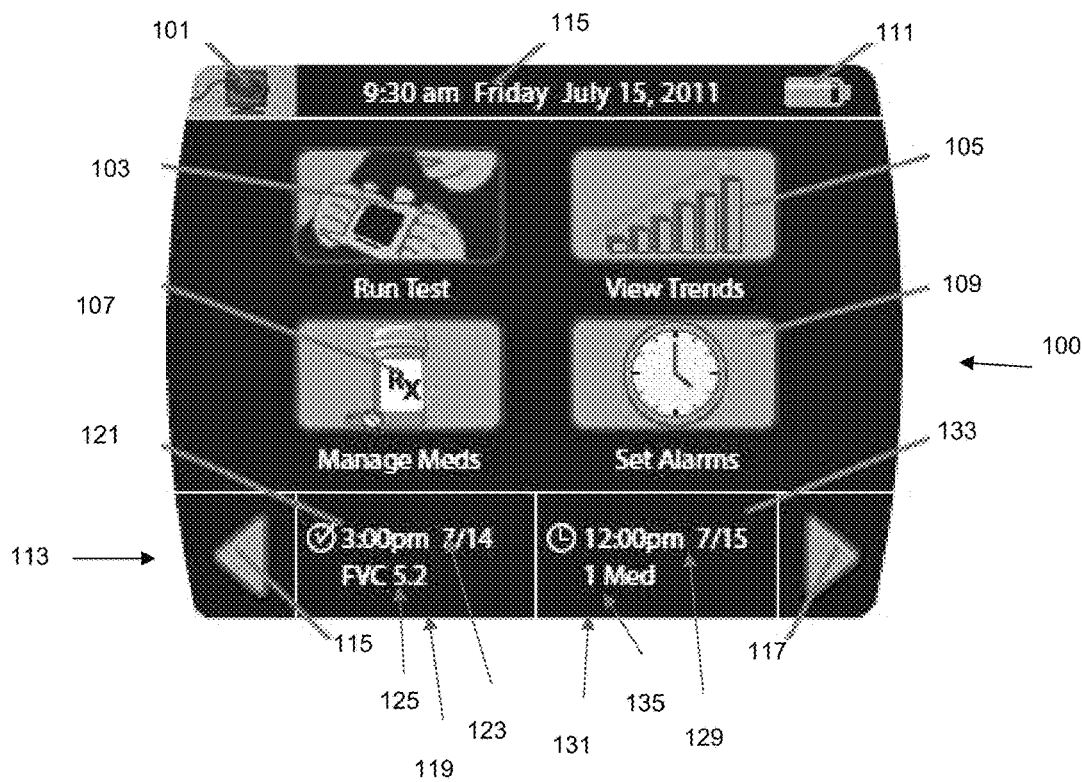
FIG. 15 is a screen shot image provided by the display screen of the spirometer illustrating an exemplary home screen.
Figure 16:
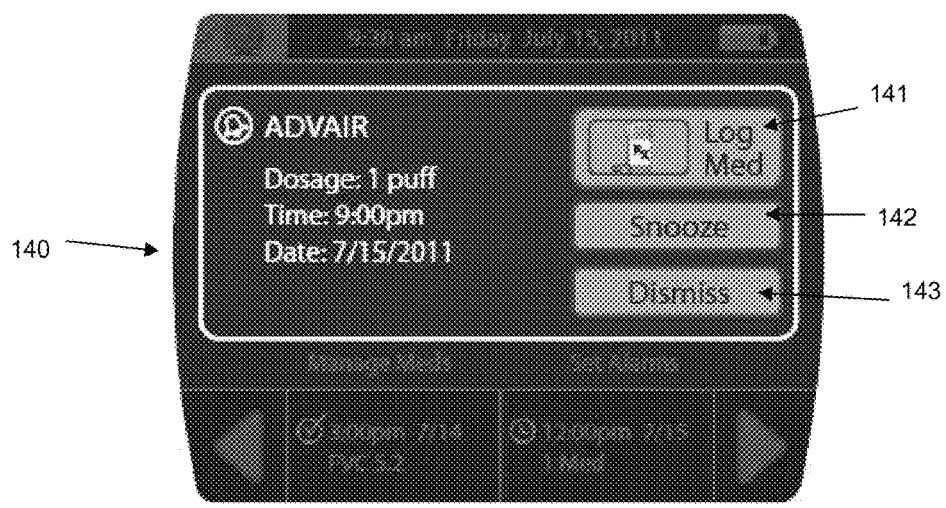
FIG. 16 is a screen shot image provided by the display screen corresponding to a medication alarm of the spirometer in accordance with the principles of the invention.

FIG. 16 illustrates an exemplary pop up screen 140 corresponding to a medication dosage. As seen, pop up alarm display 140 displays the name of the medication, the dosage, and the time and date that it should be taken. Further, it includes three buttons, namely a Log Medication button 141, a snooze button 142, and a dismiss button 143. (If the event is, instead, a spirometry test, this first button, instead, may be a Run Test button similar in appearance to the Run Test icon 103 of FIG. 15.) Touching the Log Medication button 141 will cause the device to record that the medication was taken at the date and time when the button is touched. Selecting the snooze button will cause the reminder to be snoozed for a predetermined period of time, e.g., five minutes. Touching the dismiss button 143 will cause the device to record that the medication was not taken in accordance with the reminder.

In one embodiment of the invention, the user can snooze the alarm a plurality of times. In the case of snoozed alarms, the second and subsequent repeated displays of the snoozed alarm may be color coded or otherwise visually altered each time it is redisplayed to indicate the number of times it has been delayed and/or the elapsed time since the medication should have been taken. Of course, the display need not be changed each time the particular alarm is redisplayed, but may be changed as a function of another condition such as, but not limited to, every two or three times the alarm is displayed, every additional half hour after the set alarm time. For instance, during the first hour after the initial alarm time, the display may be shown in white printing (or on a white background). In the second hour, the display may be turned green. In the third hour, the display may be turned yellow. In the fourth hour, the display may be turned red, thereby indicating the amount of delay since the medication should have been taken. In other embodiments, other display cues, such as text or icons, may be used to indicate the aforementioned delay, including, simply displaying the delay period.

Figure 17:
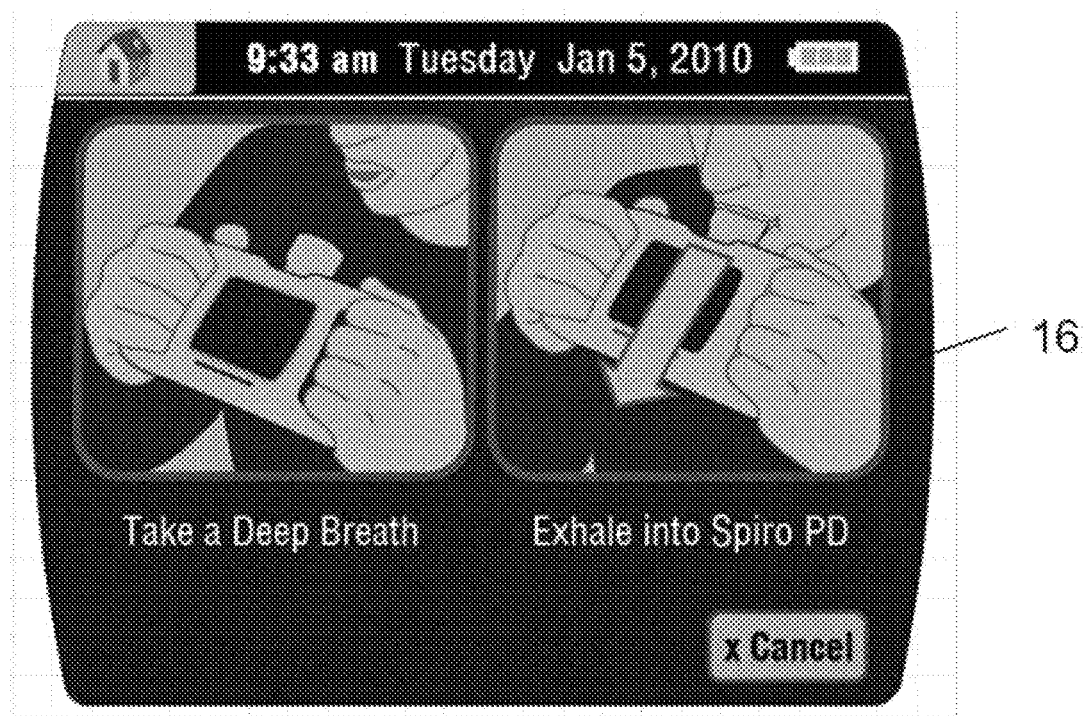
FIG. 17 is a screen shot image provided by the display screen of the spirometer providing visual instructions with respect to using the device for a lung function test run.

In another example of ergonomics, if the user presses the Run Test icon 103 in either an alarm pop-up screen (as in FIG. 16) or the home screen (FIG. 15), the Run Test screen 120 will appear as shown in FIG. 17. This screen provides instructions to the user with respect to the desired test. As shown in FIG. 17, the user is shown how to hold the spirometer and is instructed to take a deep breath and then exhale into the spirometer (or fully inhale through the spirometer depending on the test). As noted above, typically, the spirometer will require the user to take three identical tests and may instruct the user with respect to the additional tests. If any of the tests are incorrectly performed, the spirometer will provide instructions with respect to re-taking the test.

More particularly, as illustrated by FIG. 18, after each test in a test set (each testing event typically comprises performing a particular test three times and using either the best test result of the three or the average of the three tests), the user is presented with a screen indicating whether the test has been performed properly. For example, as shown, there may be three icons on the screen 161, 162, and 163 showing, for instance, a person in some stage of performing the test. Each icon corresponds to one of the three tests. If the test is performed correctly, then a check mark icon will appear in the corresponding test icon 161, 162, 163 after the test is performed indicating that the test has been performed successfully. If it is performed improperly, then a test failed icon 165 is shown instead (and the user must repeat the first test). Thus, for instance, in FIG. 18, it should be apparent that this is a display that will appear after the user has successfully performed the first two tests, as indicated by the check marks 164 in icons 161 and 162, and has unsuccessfully performed the third and final test, as illustrated by the fail icon 165 within third test icon 163. Needless to say, before a test is performed, the test icon 161, 162, or 163 is shown without a check mark 164 or a fail mark 165 in it. Alternatively or in addition, text may be provided within the display indicating whether or not the test was successful.

In one embodiment, in addition to simply indicating when a test run was unsuccessful, the microprocessor in the device may provide even more interactive coaching. In one example, the microprocessor analyzes the test result data to determine the reasons why the test was inadequate. For instance, if the test results show that the user did not exhale for a reasonably long period of time, the display screen may be caused to display a text message instructing the user to blow for a longer time on the next re-try. On the other hand, if the reason for the unsuccessful test is that the exhalation cycle was too soft, the display may instruct the user to exhale harder. Of course, such information also may be accompanied by audio, video, or multi-media instructions.

Figure 19:
FIG. 19 is a screen shot image provided by the display screen of the spirometer providing medication history data in list form.

With regard to the Manage Meds domain, a user can navigate to a View Medication history screen such as illustrated in FIG. 19. The View Medication screen is presented, for example, in list form with an entry for each scheduled dosage. Thus, as illustrated, each entry includes information for date and time, the particular medication, and the particular dose under a column heading 151, 152, and 153 corresponding to each of those pieces of information. By touching the column heading 151, 152, and 153, the user can cause the list to be displayed in order by the subject matter of the column heading. For instance, touching the date and time column heading 151 will cause the medication entries to be chronologically listed. Furthermore, the column heading by which the medication dosage information is being organized is indicated by a color change for that heading. Thus, in FIG. 19, the date and time column heading 151 is displayed in a different color from the other column headings, indicating that the medication dosage information is displayed in chronological order. As another example, if the user touches the medication heading 152, then the medication heading 152 would be highlighted and the medication information would be displayed alphabetically by the name of the medication (and secondarily in chronological order). The user can scroll up and down through the list by pressing the up and down arrows 154 and 155. Note that the events are color coded, with the events in which the user indicated that the medication was taken (e.g., by touching the Log Medication button 141 in the alarm screen 140 of FIG. 16), are displayed in a first color (e.g., green). Note that this information is duplicated by the check mark symbol in the left hand portion of the date and time column, the check mark indicating that the medication was taken. On the other hand, medication doses that were not indicated as being taken by the user are shown in a different color (e.g., red) with a different symbol, namely the clock symbol, at the left hand portion of the date and time column.

After a test set is successfully completed, including all three test trials, the best test results of the trials will be displayed on the display screen 16 of the spirometer. By way of example, this may include values for FVC, FEV1, FEV1/ FVS, FEF 25-75, and PEF. Of course, other or different values may be displayed depending upon the particular test taken, for example a value of IVC may be provided. The percentage of these test values relative to that predicted for the patient (i.e. based on age, gender, height, weight and ethnicity) can also be displayed on the screen. Further, the "severity" of each of these values can be listed (i.e. "high", "normal", "moderate", "mild", "low", "etc."). The user is also provided with additional icons with respect to uploading the data to an external host computer, viewing graphical results of the test, and viewing trend data which is a log of all test data taken to date or within a selected date range.

When the user presses the view trends icon on the touch screen display 16, the screen lists the results of all tests taken along with the time and date of each test and permits the user to scroll through the complete listing. The user can limit this listing to a particular date range, if desired. In addition, the user can limit the listing to any particular test type, such as those discussed above. Preferably, the display screen 16 is a color screen and any test result considered of a "high" severity is displayed in red or in flashing-red to draw quick attention to the particular result.

Figure 20:
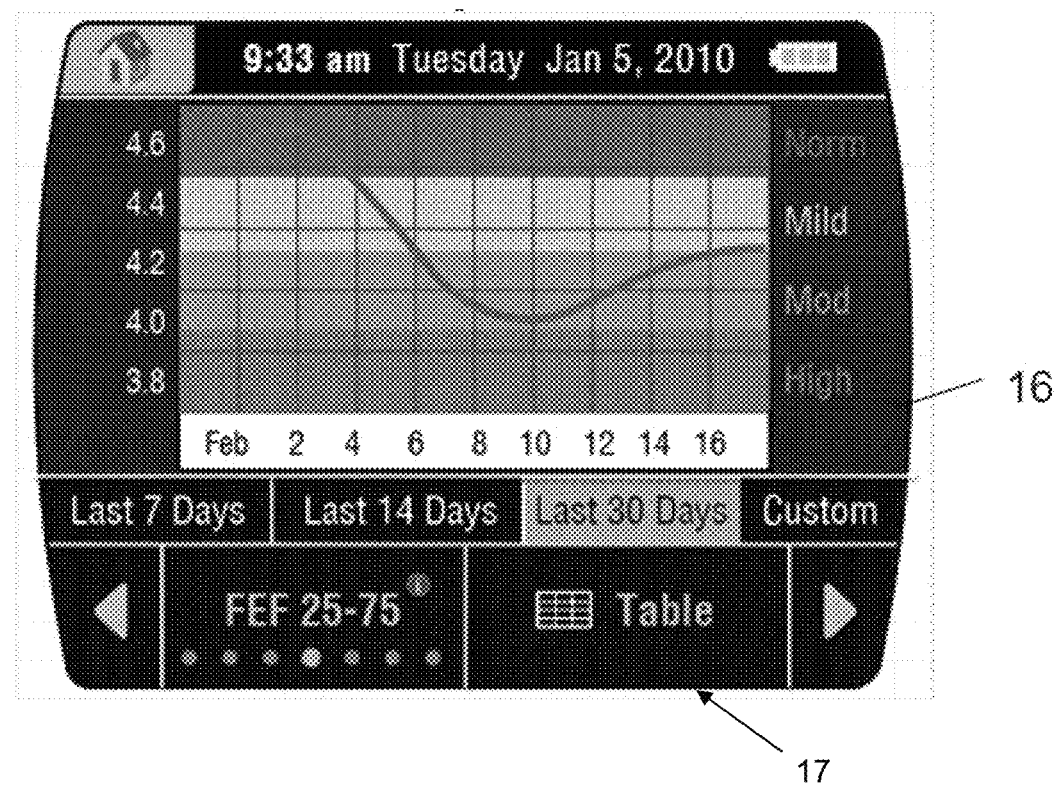
FIG. 20 is a screen shot image provided by the display screen of the spirometer providing test trend data in one graphical form.

The user can press the view graphical results for any particular test and for any particular value. For example, FIG. 20 shows the display screen 130 showing trend data for FEF 25-75 measurements in graphical form. Since the display is a color display, the different parts of the graph are color-coded. For instance, the part of the graph representing "normal" can be color-coded green, the part of the graph representing "mild" severity can be color-coded yellow, the part of the graph representing "moderate" severity can be color-coded orange, and the part of the graph representing "high" severity can be color-coded red. For example, as shown in FIG. 20, the test results were initially normal, fell to "moderate" severity, and more recently show "mild" severity.

The above style graph can be shown for any test or for any particular test values.

In addition, the user can view flow-volume loops and volume-time curves for each test. Thus, the spirometer stores a number of tests and the test results can be viewed in numerical raw data format or in graphical format.

Figure 21:
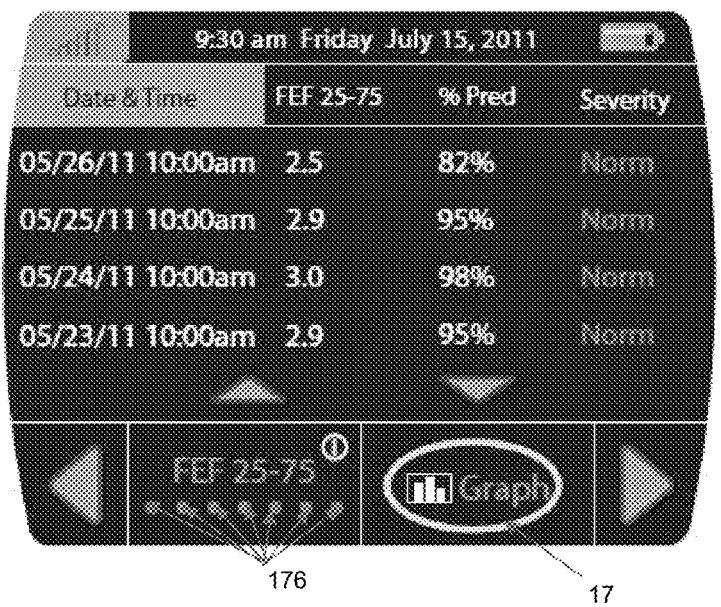
FIG. 21 is a screen shot image provided by the display screen of the spirometer of FIG. 1 providing a display of test trend data in a tabular form.

The past test data can be accessed in either a tabular format or graphically (e.g., by pressing the View Trends icon 105 in the home screen of FIG. 15). FIG. 21 shows a list of test results displayed in tabular format. Various headings, such as date and time, FEF 25-75 value, percent of predicted, and severity, may be displayed and the tests organized in either ascending or descending order by any of those columns by touching the corresponding column heading. A user may toggle between tabular and graphical formats for display of any given set of past test data by pressing toggle switch icon 171 seen in both FIGS. 20 and 21. In FIG. 21, for instance, the test data is being displayed in graphical format. So the toggle switch 171 shows the word "Table" along with a representation of a table to indicate that touching it will cause the data to be displayed in tabular format. On the other hand, when the data is being displayed in tabular format, as in FIG. 20, toggle switch 171 may have a different form, such showing the word "Graph" along with a miniature graph icon as seen in FIG. 20 to indicate that pressing the button will switch back to showing the data in a graphical format.

Figure 22:
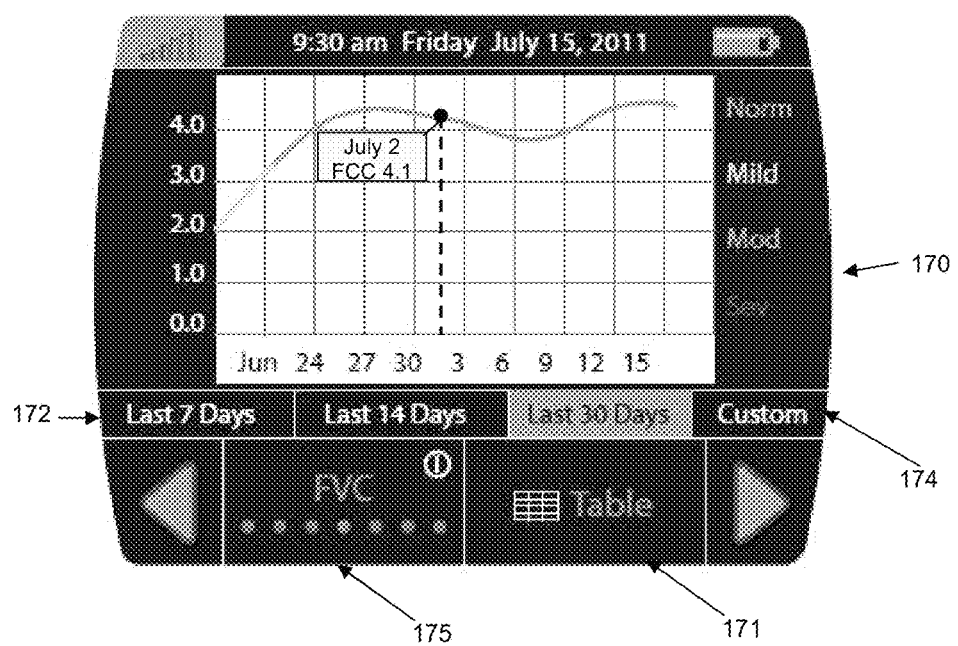
FIG. 22 is a screen shot image provided by the display screen of the spirometer providing test trend data in a second graphical form.
Figure 23:
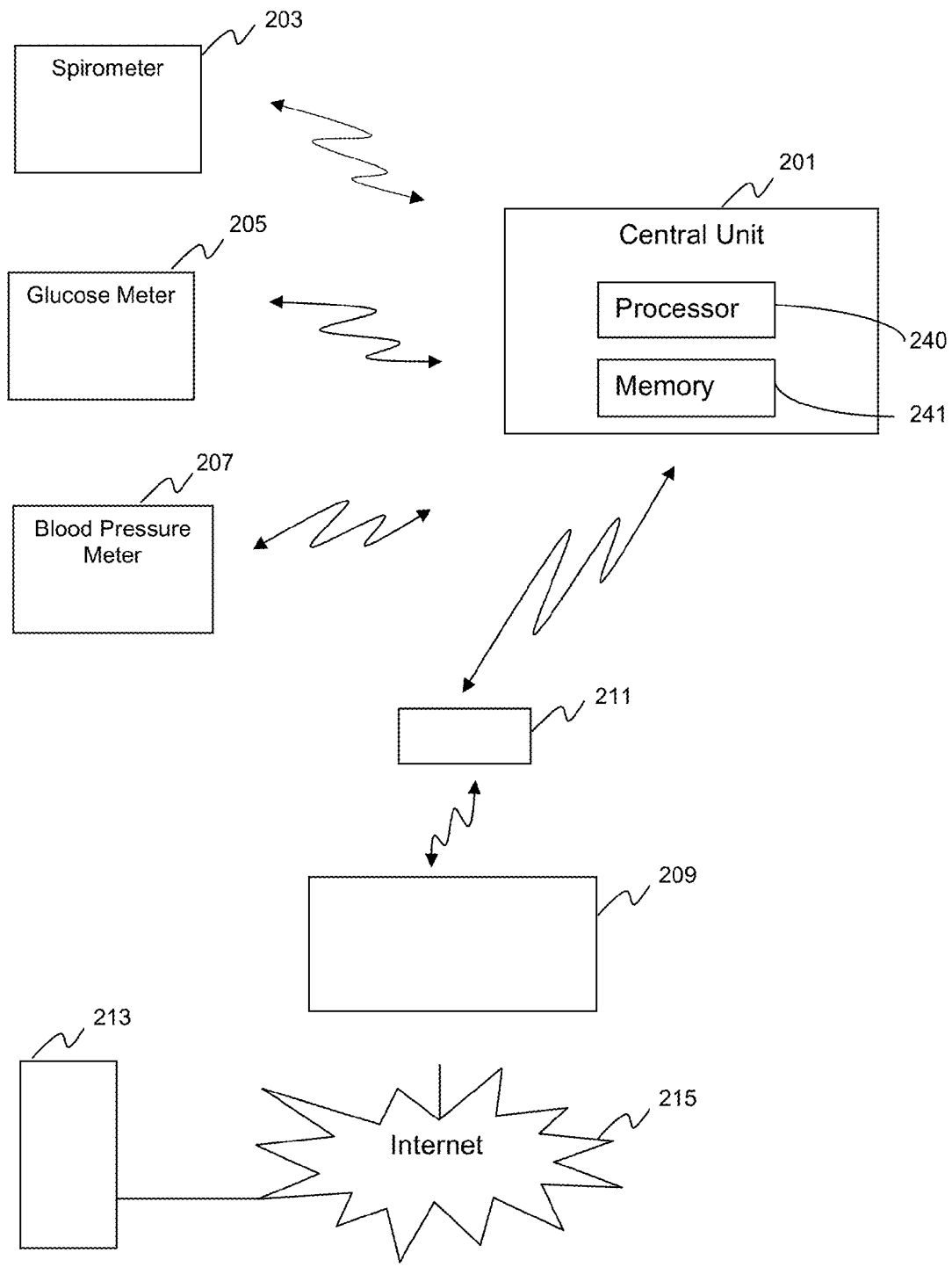
FIG. 23 is a block diagram illustrating a modular embodiment of the present invention.

FIG. 22 shows test results for a different test, namely, FVC, in graphical form, and helps illustrate an alternate embodiment for graphically displaying test data. In the graphical display of FIG. 22, the data for tests, such as FVC tests, is displayed in graphical format with the FVC value represented on the ordinate (or vertical axis) and the test instance, for example, by date and/or time, represented on the abscissa (or horizontal axis). The line 173 represents the test results. FIG. 22 shows a slightly different user-friendly way to display the severity of the results from that depicted in FIG. 21. Particularly, the line 173 is color-coded according to the test result value. Thus, portions of line 173 corresponding to test results that were within the normal range will appear green, while test results within the mild range are shown in yellow, test results in the moderate range are shown in orange, and test results in the severe range are red. Note also that the text along the right hand side of the display also indicates those ranges textually as well as by the color of the text.

In accordance with another feature, a horizontal sliver of the screen 172, lets the user choose the number of test results or days to be displayed in the particular graph, including a Custom button 174. Pressing any of the other buttons in screen portion 172 leads directly to a display corresponding to the corresponding number of days or tests indicated. Pressing the custom button, on the other hand, changes the display to a custom number of days or tests that was previously set by the user under the settings domain.

Another useful feature illustrated in FIG. 22 (also seen in FIGS. 20 and 21) is the display area 175, which includes a plurality of icons, such as dots, the number of those icons indicating the total number of pages of the displayed type of tests or other data. For instance, icon 175 in FIG. 22 shows seven dots 176 with the fourth dot highlighted or otherwise distinguished from the other dots. This indicates that there are a total of seven pages of test result data available for viewing and that the user is looking at the fourth page thereof. This same display concept is used in many other contexts and in many screens in the device. However, in the screen illustrated in FIG. 22, in which the graphical display is a graphical display of FVC trend data, the dots indicate that there are seven pages of test result data, e.g., (1) PEF trend data, (2) FEF 25-75 (the average speed of air flow during the middle part of exhalation) trend data, (3) FEV1 trend data, (4) FVC trend data, (5) FEV-1/FVC trend data, (6) lung age (the age of the subject's lungs compared to subject's actual age) trend data, and (7) all trends summary data.

This feature is very user friendly insofar as many users who are not professionals, but rather are patients, may find it difficult to interpret the data because the numbers are meaningless without previous knowledge of expectations. However, the color coding and the normal/mild/moderate/severe text are highly intuitive.

FIG. 22 illustrates yet another optional feature of the invention relating to ergonomics and convenience of use of the device. Particularly, when the device is displaying a particular screen that is within one of the top level domains corresponding to one of the icons 103, 105, 107, and 109 in the home screen of FIG. 15, an icon 169 in the upper left hand corner indicates which domain the device is within. Thus, for instance, in FIG. 22, the icon 169 is a miniature version of the Manage Meds icon 107 of the home screen of FIG. 15, indicating that the device is displaying one of the sub-screens within the Manage Meds functionality domain of the device. In one embodiment, pressing that icon will cause the device to return to the preceding screen within that domain, or, if no preceding screen within the domain, back to the home screen.

Additional features may be incorporated into the device, such as alert pop up screens responsive to poor test results. For instance, if, after an FVC test is performed and the results are in the moderate range, a pop up screen may instruct the user to increase medications. As another example, if the test results indicate a severe condition, for example two consecutive severe test results, a pop up screen may instruct the user to immediately contact his or her doctor, or to call 911.

In accordance with another feature illustrated in FIG. 22, the user may touch the graphical line 173 at any point to call up a text box providing the relevant information for that point on the graph in textual format, such as the numerical values of the abscissa and ordinate of the graph for the given point on line 173. In addition, a vertical line 177 may be displayed indicating exactly where along the abscissa the user has touched the screen. In one embodiment, the user may drag his or her finger over the line in a left or right direction and the vertical line 177 will move corresponding to the motion of the finger and text in the text box will correspondingly change to indicate the corresponding data. The text box may move equivalently with the line. A horizontal line (not shown) also may be displayed to show similar orientation relative to the ordinate axis.

In accordance with another aspect of the invention that may be provided under the View Trends top level domain, the device may present a display correlating lung function (e.g., the spirometry test results) to the medication schedule so that the user can be made directly aware of the effect of the medication on his or her lung function.

Merely as one example, a graph may be displayed similar to the graph in FIG. 22, but simultaneously showing the lung function graph line and a medication graph line. Thus, the user can directly observe the trend in lung function as a function of one or more medications, possibly being able to correlate a failure to take a scheduled dosage with a decrease in lung function. As another example, the user may be able to see a trend of improved lung function with consistent taking of a particular medication. When the user activates the Manage Meds icon 107 in the home screen (FIG. 15), the display screen provides a scrollable list of prescribed medicines along with the dosages and start and end dates. When the user selects a particular medicine, the scheduled times and dates to take the medicine are displayed. That screen also allows the user to enter a new medication to the list, check the medication schedule, view the medication history for medications already taken, and log an entry with respect to providing an acknowledgement that a medication was taken.

Additional functionality provided by the device includes a medical diary. An additional top level domain icon may be added to the home screen (FIG. 15) for medical diary functionality. Particularly, the medical diary can be a log in addition to the testing and medication history logs. This functionality may permit a user to enter additional medically relevant information that does not fit within any of the other domains at will, such as "my cough is getting worse", "I don't feel well today", or any other information that may be medically relevant. The device may automatically time and date stamp such entries upon entry (possibly, with the option of allowing the user to change the time and date stamp for the entry if the user is not entering it contemporaneously with the relevant medical information). In one embodiment, the user may be presented with a finite number of choices of medically relevant events or information to choose from in order to allow the events to be more easily categorized for purposes of use in algorithms that correlate medical data for statistical or predictive purposes. There may be a catch-all choice that allows the user to enter text for any event that does not correspond to one of the predetermined choices. In another embodiment, the user may be permitted to enter data for any event via straight textual typing and the device may be equipped with intelligence to interpret natural language text for purposes of categorization for statistical and predictive purposes.

In one embodiment, the information from any two or more of the test data, medication schedule data, and medical diary may be correlated with each other to generate and display relevant trend data that may be useful to the user. Merely as a few examples, data can be generated to illustrate any correspondence between test results and coughing fits or between the medication doses and coughing fits. In fact, in accordance with one embodiment of the invention, any or all of the test result data, medical diary data, and medication data can be processed to predict significant medical event, such as an asthma attack. The data used for such prediction may be based strictly on the historical data for the particular patient stored n the device. However, in other embodiments, the prediction may be based not only on the individual user's historical data, but also on historical data collected from other users of similar devices.

In accordance with other aspects of the invention, when the user activates the upload data icon 101 (FIG. 15), the display screen 16 provides instructions with respect to connecting a cable, such as a USB cable, to the connection port 32 of the spirometer 10 and to connect the cable to the external host computer. The particular data desired for upload can be selected and the data can be uploaded so that, for instance, the data can be viewed by a physician or the like.

In one embodiment, the spirometer is configured to compare test results with other user data and indicate a relationship if appropriate. More specifically, referring to FIG. 24, a schematic of the spirometer 250 comprising a processor 251 and memory 252 operatively connected to the processor 251. In this embodiment, the memory is configured with instructions to instruct the processor to perform the following steps: (a) record spirometer results of a user; (b) correlate the results with user data, the user data comprising at least one of a medication log, a medical diary, a baseline performance for the user provided by a healthcare provider, or other results from other testing devices; and (c) indicating a relationship between the results and the user data. In one embodiment, the user data comprises the baseline and the relationship is an alarm when the results are a certain point below the baseline performance. In one particular embodiment, the alarm comprises a recommendation to seek medial attention or a recommendation to take certain medication. In another embodiment, the user data comprises the medication log and the relationship indicates a relationship between lung function and medication taken. In yet another embodiment, the memory also comprises instructions for the processor to determine if any medicines conflict in the medical log, and, if so, to alert the user to the conflict. Still another embodiment involves the user data comprising the medication log or the medical diary and the relationship indicates the potential for a medical condition. In one embodiment, the medial diary involves a numerical ranking of the user's health and the representation comprises simultaneously displaying plots of the numerical ranking, the results and medical log compliance to indicate interrelationships. In one embodiment, the medical condition includes one of a seizure, an attack, a loss of consciousness, a fit, or an asthma attack.

It is believed that there will be an increasing number of home-use medical test devices widely available on the market, such as spirometers, blood pressure meters, and glucose meters just to name a few. In one embodiment of the invention, a system of separate modules is provided for conducting different tests, illustrated in FIG. 24. More particularly, a central unit 201 comprising a processor 240 and memory 241 is provided which comprises the display hardware and software, the data gathering hardware and software, the data processing and logging software, and any other hardware or software providing functionality that is likely to be used in connection with two or more different types of tests. The peripheral modules 203, 205, 207 contain the specific hardware and/or software that is unique to a particular test is provided in a separate module, e.g. spirometer unit 203 includes the breathing tube and turbine assembly and turbine speed detection hardware and possibly some of the software for determining the spirometry test results, or possibly only speed of the turbine or at least recording the light beam interruption data. Similar concepts would be applied to other types of testing equipment like blood pressure meter 207 and glucose meter 205. The various modules may be provided with electrical or optical ports that can be interconnected by cables to transfer data between the test modules 203, 205, 207 and the central module 201. In yet other embodiments, the various modules can be provided with Bluetooth connectivity so they can communicate with each other wirelessly.

In addition, at least the central unit 201 may be equipped with hardware and software for communicating with a home computer 209 over a Wi-Fi network, such as a home wireless network via a wireless router 211 and communication protocol, such as 802.11. Alternately, the central unit 201 or other units 203-207 may communicate with a home network through cell phone-based Bluetooth connectivity, in which a cell phone may be used as base station for a wireless hot spot. In yet other embodiments, the modules 201-207 may be equipped with cellular communication hardware and software for direct communication to a cellular network.

Yet further, software may be provided in the central unit 201 or other modules and/or on a home computer 209 for uploading relevant data to the home computer 209 and/or over the internet 215 to a data repository 213. In this manner, for instance, a central service provider can collect data from multiple users of the spirometers and other test equipment to create databases of such information and algorithms for generating useful data, such as data for predicting medical events, such as asthma attacks based on testing, medication scheduling data, and/or medical diary data as previously described. Likewise, such data and/or corresponding algorithms and other software updates can be downloaded to the central unit 201 or other modules 203-207 via the internet and/or home network connectivity.

In addition, a central provider may be able to further correlate the data collected from the users of the devices with other data from other sources, such as electronic medical records of the user's of the modules 201-207, to provide even more useful statistical data for purposes such as predicting medical events, drug efficacies, etc.

Connectivity to the internet can be used to improve the use and efficacy of such devices in many different ways. For instance, a gaming element can be added to the use of the device. For instance, points can be awarded for taking medications regularly, or obtaining certain values during testing. In other aspects, visual displays can be shown on the screen having a gaming aspect to encourage the user to perform some desirable action. For instance, in order to better encourage a person to inhale or exhale with full force, a floating ball may be displayed on the screen, with the ball reaching a bell or other goal when the user has achieved a certain level of performance. Of course, a gaming aspect does not necessarily require internet connectivity and can be incorporated fully in the on-board software of the device(s).

In yet other embodiments, performance data of an individual can be shared with other authorized individuals, such as individuals in an organized support group to which the user belongs so that the individuals in the support group can compare their results with each other and offer encouragement or help as needed. In yet other aspects, data can be shared with loved ones and caregivers over the internet so that such persons can remotely monitor the condition of a user of one of the devices.

In accordance with yet another aspect of the invention, the device may be provided with an electrical, optical, or wireless port for interfacing with a medication delivery product and directly control the dosage output of that product. Particularly, one of the major problems with medication is improper dosing by inexperienced users.

In accordance with yet another aspect of the invention, a port can be used to couple the device to a lab-on-a-chip device for processing data generated by the lab-on-a-chip and/or communicating it to others as described hereinabove.

In accordance with yet other aspects of the invention, the device may be adapted to provide even additional functionality under other top level domains offered in the home menu, including, for instance, education and exercise features. For instance, educational data, e.g., in the form of text, audio, visual, video, or multi-media, may be stored on the device or downloaded or streamed via internet connectivity for access by the user through the device. Likewise, exercise data, such as exercise instructions in either video, text, or audio, or any other form may be made available on the device either through direct storage on the device or connectivity through the device to the internet.

Figure 24:
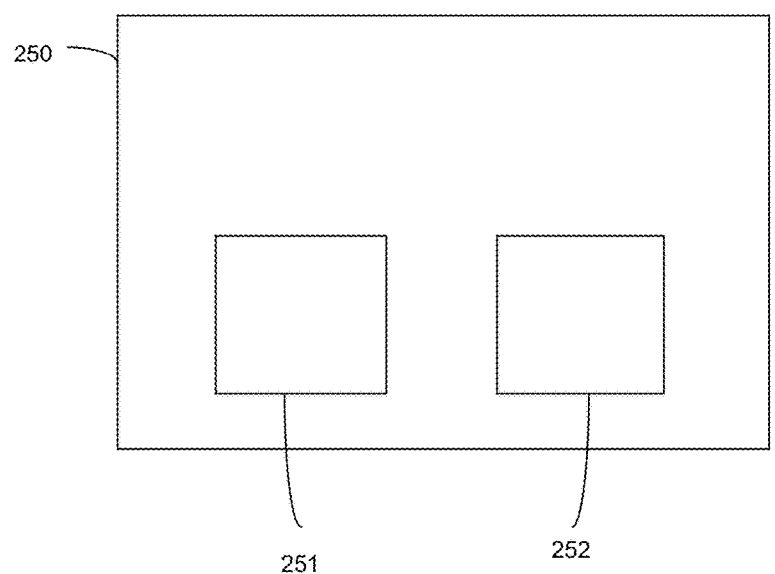
FIG. 24 is a schematic diagram of the spirometer showing the processor and memory.

In accordance with another aspect of the invention, a given device or central module of a modular system such as seen in FIG. 24 may be adapted to be used by multiple persons. In such a case, there might be an additional screen before the home screen illustrated in FIG. 15 providing the user with the option of selecting a particular individual using the device. In addition to the above, the device settings of the spirometer can be adjusted, such as, brightness of display, volume level/mute, time/daylight savings time, format of date, unit of measure (English, metric), language (English, Spanish, etc.), and font size of letters appearing in the display (large, small). The patient can also be initially prompted to enter their name, date of birth, gender, height, weight, and ethnicity and this information is saved in memory. Finally, the patient or caregiver can set up any number of alarms with respect to taking respiratory tests and/or medications at any desired time or times of day and for any days specified.

Accordingly, the user is provided with a tool that informs the patient with an alarm when to take respiratory tests and/or medications and instructions on how to take the tests. The structure of the spirometer ensures that reliable, valid, and meaningful test results are taken, and all test results are electronically stored and can be viewed in numerous formats. Test results that are considered to be of "high" severity can be displayed in red or flashing red to draw quick attention to such results. The trends of the tests over a period of time can be viewed to see if the results are improving, staying the same, or becoming worse. Medication history of medicines taken can be viewed, and a schedule of medications to be taken can be viewed. All the above can be readily uploaded into a host computer, such as a computer of a physician, so that the physician can track the progress of treatment. Also, all operations of the spirometer can be controlled via selecting icons or the like on a touch screen color display panel.

Having thus described particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A hand-held spirometer for correlating test results with a medical condition, said spirometer comprising:
   a portable housing having handles configured for said user to grip said handles to hold said housing during use;
   a display on a surface of said housing;
   an airflow tube through said housing;
   one or more air flow sensors associated with said airflow tube;
   a processor in said housing;
   memory operatively connected to said processor and configured with instructions to instruct the processor to perform the following steps:
      determining and recording sequential lung performance values based on data from said air flow sensors over a period;
      recording user data during said period, said user data comprising at least medical compliance;
      correlating said sequential lung performance values and said user data over said period; and
      displaying a relationship between said sequential lung performance data and said medical compliance over said period on said display; and wherein said relationship on said display comprises a plot of lung performance per increment of time during said period with an indication of medical compliance for each said increment of time during said period.

2. The spirometer of claim 1, further comprising correlating said sequential lung performance values with baseline performance for said user and indicating an alarm when said sequential lung performance values are a certain point below said baseline performance.

3. The spirometer of claim 2, wherein said alarm comprises a recommendation to seek medical attention or a recommendation to take certain medication.

4. The spirometer of claim 1, wherein said memory also comprises instructions for said processor to determine if any medicines conflict in the medical log, and, if so, to alert said user to said conflict.

5. The spirometer of claim 1, wherein said user data further comprises a medical diary and said relationship indicates the potential for a medical condition.

6. The spirometer of claim 5, wherein said medical diary involves a numerical scale of the user's health.

7. The spirometer of claim 5, wherein said medical condition includes one of a seizure, an attack, a loss of consciousness, a fit, or an asthma attack.

8. The spirometer of claim 7, wherein said indication includes a warning to seek medical attention immediately or to take medication.

9. The spirometer of claim 1, wherein said user data is entered by said user.

10. The spirometer of claim 9, wherein said user data is transmitted electronically from a separate device to said spirometer.

11. The spirometer of claim 10, wherein said user data is transmitted wirelessly.

12. The spirometer of claim 1, wherein said user data further comprises data from other devices.

13. The spirometer of claim 1, wherein said period is over a week.

14. The spirometer of claim 1, wherein said period is over a week and said time increment is a day.

* * * * *